(12) United States Patent
Bigg et al.

(10) Patent No.: US 7,192,975 B2
(45) Date of Patent: Mar. 20, 2007

(54) ARYLIMIDAZOLE DERIVATIVES, PREPARATION AND THERAPEUTIC USED THEREOF

(75) Inventors: Dennis Bigg, Gif-sur-Yvette (FR); Anne-Marie Liberatore, Auffargis (FR); Pierre-Etienne Chabrier De Lassauniere, Paris (FR)

(73) Assignee: Societe de Conseils de Recherches Et d''Applications Scientifiques (S.C.R.A.S.) (FR)

( * ) Notice: Subject to any disclaimer, the term of this patent is extended or adjusted under 35 U.S.C. 154(b) by 178 days.

(21) Appl. No.: 10/517,267

(22) PCT Filed: Jul. 24, 2003

(86) PCT No.: PCT/FR03/02336

§ 371 (c)(1),
(2), (4) Date: Dec. 6, 2004

(87) PCT Pub. No.: WO2004/011402

PCT Pub. Date: Feb. 5, 2004

(65) Prior Publication Data

US 2005/0234118 A1 Oct. 20, 2005

(30) Foreign Application Priority Data

Jul. 25, 2002 (FR) .................... 02 09416

(51) Int. Cl.
*A61K 31/4178* (2006.01)
*C07D 409/12* (2006.01)
(52) U.S. Cl. ............... 514/397; 548/315.1; 548/336.5; 548/338.1; 548/335.5
(58) Field of Classification Search ............. 548/315.1, 548/336.5, 338.1, 335.5; 514/397
See application file for complete search history.

(56) References Cited

U.S. PATENT DOCUMENTS 4,666,932 A * 5/1987 Cereda et al. ............. 514/400

FOREIGN PATENT DOCUMENTS

WO  WO 98/58934    12/1998
WO  WO 01/26656 A2  4/2001

OTHER PUBLICATIONS

Smith et al., The Lancet Neurology, Aug. 2002, 1(4), pp. 232-241.*

* cited by examiner

*Primary Examiner*—Laura L. Stockton
(74) *Attorney, Agent, or Firm*—Charles A. Muserlian

(57) ABSTRACT

Compounds of the formula

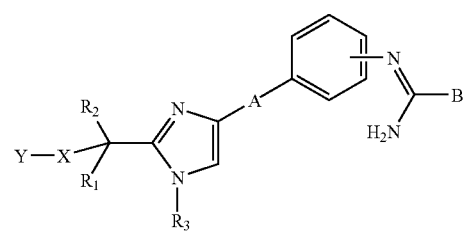

wherein the substituents are as defined in the specification which are useful for the treatment of pain.

7 Claims, No Drawings

ARYLIMIDAZOLE DERIVATIVES, PREPARATION AND THERAPEUTIC USED THEREOF

This application is a 372 of PCT/FR2003002336 FILED Jul. 24, 2003.

The present Application relates to novel arylimidazole derivatives which can be used as NO synthase (NOS) inhibitors and as sodium channel modulators.

Given the potential role of NO and the sodium channels in physiopathiology, the new derivatives described corresponding to general formula (I) described hereafter can produce beneficial or favourable effects:

in the treatment or prevention of pain, and in particular:
  neuropathic pain and in particular:
    neuropathic pain of metabolic origin (such as for example the diabetic neuropathies),
    neuropathic pain of infectious origin such as those linked with viral or retroviral diseases (such as for example pain linked with herpes such as post-herpetic pain, pain linked with Acquired Immune Deficiency Syndrome (AIDS) or pain linked with herpes zoster),
    neuropathic pain of traumatic origin (such as for example those linked with a phantom limb)
  glosso-pharyngeal neuralgia, secondary metastatic infiltration radiculopathies and neuropathies, adiposis dolorosa and pain linked with burns,
  migraine,
  post-operative pain,
  central pain following vascular cerebral accidents, thalamic lesions or multiple sclerosis,
  chronic pain, and
  pain linked with cancer;
in the treatment of multiple sclerosis;
in the treatment of disorders of the central or peripheral nervous system and in particular:
  epilepsy,
  neurodegenerative diseases, of which senile dementia can in particular be mentioned, including Alzheimer's disease, Huntington's chorea, Parkinson's disease, amyotrophic lateral sclerosis, Friedreich's ataxia and prion diseases (in particular Creutzfeld Jacob's disease),
  cerebral ischaemia and cerebral and spinal cord traumatisms.
  depression and bipolar disorders,
  encephalopathies, including encephalopathies of viral or toxic origin,
  addiction to opiates, alcohol and addictive substances,
  erective and reproductive disorders,
  cognitive disorders,
  anxiety, schizophrenia, sleep disorders and eating disorders (anorexia, bulimia, etc.);
in the treatment of the cardio vascular disorders such as myocardial infarction or disordered cardiac rhythms, more particularly arrhythmia;
in the treatment of disorders of the skeletal muscle and neuromuscular joints such as myopathies;
in the treatment of inflammatory diseases such as for example psoriasis, arthrosis and rheumatoid arthritis, inflammations of the gastrointestinal system (colitis, Crohn's disease) or of the pulmonary system and airways (asthma, sinusitis, rhinitis) as well as contact or delayed hypersensitivities, and in particular arthrosis and rheumatoid arthritis;
in the treatment of hearing losses of traumatic, acoustic or toxic origin and tinnitus.
in the treatment of complications linked to auto-immune and viral diseases such as for example lupus, AIDS, parasitic and viral infections, diabetes complications including retinopathies, nephropathies and polyneuropathies;
in the treatment of neurological diseases associated with intoxication (Cadmium poisoning, inhalation of n-hexane, pesticide, herbicide), with treatments (radiotherapy) or disorders of genetic origin (Wilson's disease);
and more generally in the treatment of all pathologies characterized by excessive production of nitrogen monoxide and/or a dysfunction of the sodium channels.

The Applicant had described in the Application WO01/26656 derivatives of imidazoles which can modulate the sodium channels, namely the compounds of general formula (A1)

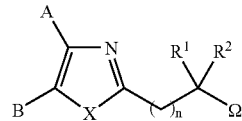

(A1)

in which:
  A represents (in particular) an optionally substituted phenyl or biphenyl radical;
  B represents (in particular) a hydrogen atom or an alkyl radical;
  X represents (in particular) $NR^{38}$, $R^{38}$ representing in particular a hydrogen atom or an alkyl or aralkyl radical;
  n is an integer from 0 to 6;
  Ω represents one of the $NR^{46}R^{47}$ or $OR^{48}$ radicals in which $R^{46}$ and $R^{47}$ represent (in particular), independently, a hydrogen atom or an alkyl, aryl, aralkyl, cycloalkyl or cycloalkylalkyl radical and $R^{48}$ represents a hydrogen atom or an alkyl radical.

These compounds did not however present any activity vis-à-vis NOS such as that of the compounds of the invention.

Moreover, a subject of Application WO95/05363 is NOS-inhibiting compounds of general formula (A2)

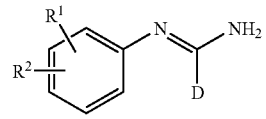

(A2)

in which:
D represents phenyl, pyridinyl or an aromatic heterocycle with 5 members containing from 1 to 4 heteroatoms chosen from O, N and S, these three groups being optionally substituted by one or more groups chosen from $(C_1–C_6)$alkyl, $(C_1–C_6)$alkoxy, halogen, $(C_1–C_6)$perfluoroalkyl, or D represents $(C_1–C_6)$perfluoroalkyl;

$R^1$ represents hydrogen;

$R^2$ represents —X(CH$_2$)$_n$ZCONR$^3$R$^4$, —X(CH$_2$)$_n$NHCO(CH$_2$)$_s$NR$^3$R$^4$, —X(CH$_2$)$_n$NHCOR$^5$ or —(CH$_2$)$_q$NHC(NH)R$^6$, $R^3$ and $R^4$ represent independently hydrogen, (C$_1$–C$_6$)alkyl, —(CH$_2$)$_r$—A, —(CH$_2$)$_m$OA, or —CH(CH$_3$)(CH$_2$)$_t$A;

or the group NR$^3$R$^4$ represents 1-indanyl, piperonylamino, piperidynyl, morpholinyl, pyrrolidinyl, 1,2,3,4-tetrahydroisoquinolinyl or piperazinyl optionally substituted in position 4 by (C$_1$–C$_6$)alkyl;

$R^5$ represents (C$_1$–C$_6$)alkyl, (C$_1$–C$_6$)perfluoroalkyl, —(CH$_2$)$_r$A or —O(CH$_2$)$_w$A;

A represents phenyl, pyridinyl, pyrimidinyl or an aromatic heterocycle with 5 members containing from 1 to 4 heteroatoms chosen from O, N and S, these 4 groups being optionally substituted by one or more groups chosen from (C$_1$–C$_6$)alkyl, halogen, nitro, cyano and trifluoromethyl;

$R^6$ represents phenyl, pyridinyl or an aromatic heterocycle with 5 members containing from 1 to 4 heteroatoms chosen from O, N and S, these three groups being optionally substituted by one or more groups chosen from (C$_1$–C$_6$)alkyl, (C$_1$–C$_6$)alkoxy, halogen, (C$_1$–C$_6$)perfluoroalkyl, or $R^6$ represents (C$_1$–C$_6$) perfluoroalkyl;

n and r represent independently integers from 0 to 6;

p and w represent independently integers from 1 to 5;

m represents an integer from 2 to 5;

q and t represent independently integers from 0 to 5;

s represents an integer from 1 to 3;

X represents O or a bond;

Z represents O, NR$^7$ or a bond;

$R^7$ represents hydrogen or (C$_1$–C$_6$) alkyl:

it being understood that:

(a) D, when it contains a heteroatom, is not linked to the remainder of the compound of formula (A2) by the heteroatom;

(b) when $R^2$ represents —X(CH$_2$)$_n$ZCONR$^3$R$^4$ and neither X nor Z represents a bond, then n represents an integer from 2 to 6;

(c) when $R^2$ represents —X(CH$_2$)$_n$NHCO(CH$_2$)$_s$NR$^3$R$^4$ or —X(CH$^2$)$_n$NHCOR$^5$ and X represents O, then n represents an integer from 2 to 6;

(d) when $R^2$ represents —X(CH$_2$)$_p$NR$^3$R$^4$ and X represents O, then p represents an integer from 2 to 5;

(e) when $R^2$ represents —(CH$_2$)$_q$NHC(NH)R$^6$, $R^1$ represents hydrogen, D represents phenyl and $R^6$ represents phenyl, then q does not represent 0;

(f) when $R^2$ represents —(CH$_2$)$_q$NHC(NH)R$^6$, $R^1$ represents hydrogen, D and $R^6$ represent 2-chlorophenyl, then q does not represent 0;

(g) when $R^2$ represents —(CH$_2$)$_q$NHC(NH)R$^6$, $R^1$ represents hydrogen, D and $R^6$ represent 3-pyridinyl, then q does not represent 0; and (h) when $R^2$ represents —(CH$_2$)$_q$NHC(NH)R$^6$, $R^1$ represents hydrogen, D and $R^6$ represent 4-pyridinyl, then q does not represent 0.

However, no activity vis-à-vis the sodium channels has been described for the compounds of general formula (A2).

The Applicant has now developed a new class of arylimidazole derivatives, which correspond to general formula (I)

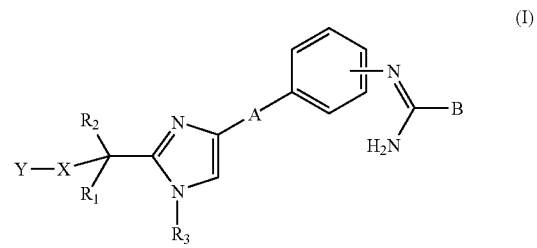

in which $R_1$ represents a hydrogen atom or an alkyl, cycloalkyl, cycloalkylalkyl radical, or also one of the aryl or aralkyl radicals, the aromatic ring of which is optionally substituted from once to 3 times (and in particular from once to twice) by substituents chosen independently from a halogen atom and an alkyl or alkoxy radical;

$R_2$ represents a hydrogen atom or an alkyl radical;

$R_3$ represents a hydrogen atom or an alkyl or aralkyl radical:

X represents a bond or a linear or branched alkylene radical containing from 1 to 5 carbon atoms;

Y represents a hydrogen atom, a cycloalkyl radical, an NR$_4$R$_5$, OR$_{14}$ or SR$_{15}$ radical or a

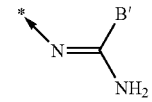

radical, or also Y represents an aryl radical optionally substituted from once to 3 times (and in particular from once to twice) by substituents chosen independently from a halogen atom and an alkyl or alkoxy radical;

A represents a bond or the phenylene radical;

B and B' are chosen independently from an alkyl radical, a cycloalkyl radical, an NR$_6$R$_7$ or SR$_8$ radical, a carbocyclic aryl radical or a heterocyclic aryl radical with 5 or 6 members containing from 1 to 4 heteroatoms chosen from O, S and N (in particular the thiophene, furane, pyrrole or thiazole radicals, and in particular the 2-thienyl radical), said carbocyclic and heterocyclic aryl radicals being optionally substituted by one to three groups chosen independently from the alkyl, alkenyl or alkoxy radicals (and in particular by a radical chosen from the methyl and methoxy radicals), $R_4$ represents a hydrogen atom or an alkyl, cycloalkyl, cycloalkylalkyl, —C(O)R$_9$, —C(O)OR$_9$, —C(O)NHR$_9$ or —SO$_2$R$_9$ radical, or also one of the aryl or aralkyl radicals, the aromatic ring of which is optionally substituted from once to 3 times (and in particular from once to twice) by substituents chosen independently from a halogen atom and an alkyl or alkoxy radical, or R$_4$ represents a bis-phenylalkyl radical, R$_5$ represents a hydrogen atom or an alkyl, aryl or aralkyl radical, or also R$_4$ and R$_5$ form with the nitrogen atom which carries them a non-aromatic heterocycle with five to seven members containing 1 to 2 heteroatoms, the elements for completing the heterocycle being chosen independently from a group comprising —CHR$_{10}$—, —NR$_{11}$—, —O— and —S—;

$R_6$ and $R_7$ represent independently a hydrogen atom or an alkyl, alkenyl or alkynyl radical, or R$_6$ represents a nitro radical and R$_7$ represents a hydrogen atom, or also R$_6$ and R$_7$ form with the nitrogen atom which carries them a non-aromatic heterocycle with five to six members, the elements for completing the heterocycle being chosen independently from a group comprising —CH$_2$—, —NR$_{12}$—, —O— and —S—;

R$_8$ represents a linear or branched alkyl radical having 1 to 6 carbon atoms optionally substituted from once to 3 times (and in particular from once to twice) by one or more substituents chosen independently from a halogen atom and the —OH, amino, cyano and aryl radicals;

R$_9$ represents an alkyl, haloalkyl, cycloalkyl or cycloalkylalkyl radical, or also one of the carbocyclic or heterocyclic aralkyl or aryl radicals, the aromatic ring of which is optionally substituted from once to 3 times (and in particular from once to twice) by substituents chosen independently from a halogen atom and an alkyl or alkoxy radical;

R$_{10}$ represents a hydrogen atom or an alkyl or aryl radical optionally substituted from once to 3 times (and in particular from once to twice) by substituents chosen independently from a halogen atom and an alkyl or alkoxy radical (R$_{10}$ being preferably chosen from a hydrogen atom or a methyl or phenyl radical), R$_{11}$ represents a hydrogen atom, an alkyl radical, a cycloalkyl radical, a cycloalkylalkyl radical, a —C(O)R$_{13}$ radical, a —C(O)OR$_{13}$ radical, an —SO$_2$R$_{13}$ radical, a —C(O)NHR$_{13}$ radical, or also one of the aryl or aralkyl radicals the aromatic ring of which is optionally substituted from once to 3 times (and in particular from once to twice) by substituents chosen independently from a halogen atom and an alkyl or alkoxy radical;

R$_{12}$ represents a hydrogen atom or an alkyl radical;

R$_{13}$ represents an alkyl radical, a haloalkyl radical or also one of the carbocyclic or heterocyclic aralkyl or aryl radicals, the aromatic ring of which is optionally substituted from once to 3 times (and in particular from once to twice) by substituents chosen independently from a halogen atom and an alkyl or alkoxy radical;

R$_{14}$ represents an alkyl radical, the phenyl radical or an aralkyl radical; and finally R$_{15}$ represents an alkyl radical, the phenyl radical or an aralkyl radical;

or are pharmaceutically acceptable salts of compounds of general formula (I).

Said compounds of general formula (I) or their pharmaceutically acceptable salts can be used for preparing a medicament intended to inhibit the NOS and to modulate the sodium channels.

In particular, the compounds of general formula (I) or the pharmaceutically acceptable salts of compounds of general formula (I) are compounds of general formula (I')

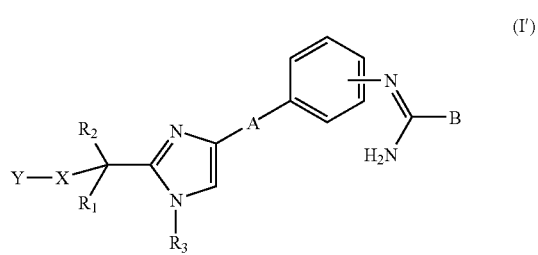

(I')

in which

R$_1$ represents a hydrogen atom or an alkyl, cycloalkyl, cycloalkylalkyl radical, or also one of the aryl or aralkyl radicals, the aromatic ring of which is optionally substituted from once to 3 times (and in particular from once to twice) by substituents chosen independently from a halogen atom and an alkyl or alkoxy radical;

R$_2$ represents a hydrogen atom or an alkyl radical;

R$_3$ represents a hydrogen atom or an alkyl or aralkyl radical:

X represents a bond or a linear or branched alkylene radical containing from 1 to 5 carbon atoms;

Y represents a hydrogen atom, a cycloalkyl radical, an NR$_4$R$_5$ radical or a

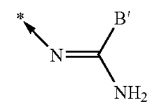

radical, or also Y represents an aryl radical optionally substituted from once to 3 times (and in particular from once to twice) by substituents chosen independently from a halogen atom and an alkyl or alkoxy radical;

A represents a bond or the phenylene radical;

B and B' are chosen independently from an alkyl radical, a cycloalkyl radical, an NR$_6$R$_7$ or SR$_8$ radical, a carbocyclic aryl radical or a heterocyclic aryl radical with 5 or 6 members containing from 1 to 4 heteroatoms chosen from O, S and N (in particular the thiophene, furane, pyrrole or thiazole radicals, and in particular the 2-thienyl radical), said carbocyclic and heterocyclic aryl radicals being optionally substituted by one to three groups chosen independently from the alkyl, alkenyl or alkoxy radicals (and in particular by a radical chosen from the methyl and methoxy radicals), R$_4$ represents a hydrogen atom or an alkyl, cycloalkyl, cycloalkylalkyl, —C(O)R$_9$, —C(O)OR$_9$, —C(O)NHR$_9$ or —SO$_2$R$_9$ radical, or also one of the aryl or aralkyl radicals, the aromatic ring of which is optionally substituted from once to 3 times (and in particular from once to twice) by substituents chosen independently from a halogen atom and an alkyl or alkoxy radical, R$_5$ represents a hydrogen atom or an alkyl, aryl or aralkyl radical, or also R$_4$ and R$_5$ form with the nitrogen atom which carries them a non-aromatic heterocycle with five to seven members containing 1 to 2 heteroatoms, the elements for completing the heterocycle being chosen independently from a group comprising —CHR$_{10}$—, —NR$_{11}$—, —O— and —S—;

R$_6$ and R$_7$ represent independently a hydrogen atom or an alkyl, alkenyl or alkynyl radical, or R$_6$ represents a nitro radical and R$_7$ represents a hydrogen atom, or also R$_6$ and R$_7$ form with the nitrogen atom which carries them a non-aromatic heterocycle with five to six members, the elements for completing the heterocycle being chosen independently from a group comprising —CH$_2$—, —NR$_{12}$—, —O— and —S—;

R$_8$ represents a linear or branched alkyl radical having 1 to 6 carbon atoms optionally substituted from once to 3 times (and in particular from once to twice) by one or more substituents chosen independently from a halogen atom and the —OH, amino, cyano and aryl radicals;

R$_9$ represents an alkyl, haloalkyl, cycloalkyl or cycloalkylalkyl radical, or also one of the carbocyclic or heterocyclic aralkyl or aryl radicals, the aromatic ring of which is optionally substituted from once to 3 times (and in particular from once to twice) by substituents chosen independently from a halogen atom and an alkyl or alkoxy radical;

$R_{10}$ represents a hydrogen atom or an alkyl or aryl radical optionally substituted from once to 3 times (and in particular from once to twice) by substituents chosen independently from a halogen atom and an alkyl or alkoxy radical ($R_{10}$ being preferably chosen from a hydrogen atom or a methyl or phenyl radical), $R_{11}$ represents a hydrogen atom, an alkyl radical, a cycloalkyl radical, a cycloalkylalkyl radical, a —C(O)$R_{13}$ radical, a —C(O)O$R_{13}$ radical, an —SO$_2$$R_{13}$ radical, a —C(O)NHR$_{13}$ radical, or also one of the aryl or aralkyl radicals the aromatic ring of which is optionally substituted from once to 3 times (and in particular from once to twice) by substituents chosen independently from a halogen atom and an alkyl or alkoxy radical;

$R_{12}$ represents a hydrogen atom or an alkyl radical; and finally $R_{13}$ represents an alkyl radical, a haloalkyl radical or also one of the carbocyclic or heterocyclic aralkyl or aryl radicals, the aromatic ring of which is optionally substituted from once to 3 times (and in particular from once to twice) by substituents chosen independently from a halogen atom and an alkyl or alkoxy radical;

or are pharmaceutically acceptable salts of compounds of general formula (I').

By alkyl, unless otherwise specified, is meant a linear or branched alkyl radical containing from 1 to 12 carbon atoms, preferably from 1 to 8 carbon atoms and still more preferentially from 1 to 6 carbon atoms. By cycloalkyl, unless otherwise specified, is meant a cycloalkyl radical containing from 3 to 7 carbon atoms. By alkoxy, unless otherwise specified, is meant an alkoxy radical the carbon chain of which is linear or branched and comprises from 1 to 6 carbon atoms. By alkenyl, unless otherwise specified, is meant a linear or branched hydrocarbon radical containing 2 to 6 carbon atoms and at least one double bond. By alkynyl, unless otherwise specified, is meant a linear or branched hydrocarbon radical containing from 2 to 6 carbon atoms and at least one triple bond. By haloalkyl is meant an alkyl radical at least one (and optionally all) of the hydrogen atoms of which is replaced by a halogen atom. By haloalkoxy is meant an alkoxy radical at least one (and optionally all) of the hydrogen atoms of which is replaced by a halogen atom. By carbocyclic or heterocyclic aryl, unless otherwise specified, is meant a carbocyclic or heterocyclic system comprising from one to three condensed rings at least one of which is an aromatic ring and all are rings with 5 to 7 members, a system being called heterocyclic when at least one of the rings which make it up comprises one or more heteroatoms (O, N or S). By aryl, unless otherwise specified, is meant a carbocyclic aryl radical. Finally by halogen atom is meant an atom chosen from fluorine, chlorine, bromine and iodine atoms.

By cycloalkylalkyl, aralkyl, alkoxycarbonyl, haloalkoxycarbonyl or aralkoxycarbonyl radicals is meant respectively the cycloalkylalkyl, aralkyl, alkoxycarbonyl, haloalkoxycarbonyl or aralkoxycarbonyl radicals, of which the alkyl, alkoxy, haloalkyl, cycloalkyl and aryl radicals which make them up have the meanings indicated previously.

By linear or branched alkyl having 1 to 6 carbon atoms is meant in particular the methyl, ethyl, propyl, isopropyl, butyl, isobutyl, sec-butyl and tert-butyl, pentyl, neopentyl, isopentyl, hexyl, isohexyl radicals. By cycloalkyl is meant in particular the cyclopropyl, cyclobutyl, cyclopentyl and cyclohexyl radicals. By alkoxy is meant preferably the methoxy, ethoxy, propoxy, isopropoxy, isobutoxy, sec-butoxy and tert-butoxy radicals and more preferentially the methoxy and ethoxy radicals. By haloalkyl is meant in particular the trifluoromethyl radical. By haloalkoxy is meant in particular the trifluoromethoxy radical. By carbocyclic aryl is meant in particular the phenyl, naphthyl and phenantryl radicals, preferably the phenyl and naphthyl radicals and more preferentially the phenyl radical. By heterocyclic aryl is meant in particular the pyrrolyl, furanyl, thienyl, pyridyl, pyrimidinyl, triazinyl, imidazolyl, oxazolyl, thiazolyl, indolyl and quinolyl radicals. By aralkyl is meant in particular a phenalkyl radical, and preferably the benzyl radical.

By pharmaceutically acceptable salt is meant in particular the addition salts with inorganic acids such as hydrochloride, hydrobromide, hydroiodide, sulphate, phosphate, diphosphate and nitrate or with organic acids such as acetate, maleate, fumarate, tartrate, succinate, citrate, lactate, methanesulphonate, p-toluenesulphonate, pamoate and stearate. For other examples of pharmaceutically acceptable salts, reference can be made to "Salt selection for basic drugs", *Int. J. Pharm.* (1986), 33, 201–217.

Moreover, by convention, when there is an arrow emanating from a chemical structure, pointing to an asterisk (*), said arrow indicates the attachment point. For example:

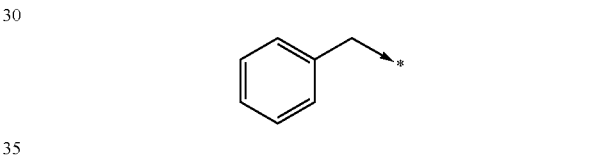

represents the benzyl radical.

Generally, the case in which A represents a bond is preferred. Similarly, the compounds in which $R_3$ represents a hydrogen atom or a methyl or benzyl radical (and in particular the compounds in which $R_3$ represents a hydrogen atom) are generally preferred.

Preferably moreover, the compounds of general formula (I) according to the invention are such that they comprise at least one of the following characteristics:

X represents a bond or a linear or branched alkylene radical containing from 1 to 5 carbon atoms (and preferably from 1 to 3 carbon atoms) and Y represents an NR$_4$R$_5$ radical;

X represents a bond or a linear or branched alkylene radical containing from 1 to 5 carbon atoms (and preferably from 1 to 3 carbon atoms) and Y represents a

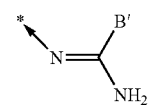

radical;

X represents a bond or a linear or branched alkylene radical containing from 1 to 5 carbon atoms (and preferably from 1 to 3 carbon atoms) and Y represents a cycloalkyl radical or an aryl radical optionally substituted from once to 3 times (and in particular from once to twice) by substituents chosen independently from a halogen atom and an alkyl or alkoxy radical;

X represents a bond and Y represents a hydrogen atom whilst at least one of $R_1$ and $R_2$ represents a radical chosen from the alkyl, cycloalkyl or cycloalkylalkyl radicals.

According to one of the preferred variants, namely when X represents a bond or a linear or branched alkylene radical containing from 1 to 5 carbon atoms (and preferably from 1 to 3 carbon atoms and still more preferentially from 1 to 2 carbon atoms) and Y represents an $NR_4R_5$ radical, it is moreover preferable for the compounds of general formula (I) according to the invention to be such that they comprise at least one of the following characteristics:

$R_4$ represents an alkyl, cycloalkyl, cycloalkylalkyl radical or also one of the aryl or aralkyl radicals, the aromatic ring of which is optionally substituted from once to 3 times by substituents chosen independently from a halogen atom and an alkyl or alkoxy radical ($R_4$ also representing more preferentially a radical chosen from the alkyl and cycloalkyl radicals and still more preferentially a cycloalkyl radical), and $R_5$ represents a hydrogen atom or an alkyl radical (and more preferentially a hydrogen atom or the methyl radical);

$R_4$ represents a —C(O)$R_9$, —C(O)O$R_9$, —C(O)NH$R_9$ or —SO$_2R_9$ radical (and quite particularly a —C(O)O$R_9$ radical) and $R_5$ represents a hydrogen atom or a methyl or ethyl radical (and preferably a hydrogen atom or the methyl radical).

According to another preferred variant, namely when X represents a bond or a linear or branched alkylene radical containing from 1 to 5 carbon atoms (and preferably from 1 to 3 carbon atoms) and Y represents a

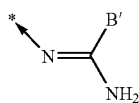

radical,
it is moreover preferable for the compounds of general formula (I) according to the invention to be such that they comprise at least one of the following characteristics:

X represents a bond or a —CH$_2$— or —(CH$_2$)$_2$— radical;
$R_1$ and $R_2$ represent hydrogen atoms.

Still according to one of the preferred variants, namely when X represents a bond or a linear or branched alkylene radical containing from 1 to 5 carbon atoms (and preferably from 1 to 3 carbon atoms) and Y represents a cycloalkyl radical or an aryl radical optionally substituted from once to 3 times (and in particular from once to twice) by substituents chosen independently from a halogen atom and an alkyl or alkoxy radical, it is moreover preferable for the compounds of general formula (I) according to the invention to be such that they comprise at least one of the following characteristics:

Y is a cyclohexyl radical;
Y is a phenyl radical optionally substituted from once to 3 times (and in particular from once to twice) by substituents chosen independently from a halogen atom and an alkyl or alkoxy radical (and preferably from a halogen atom and a methyl or methoxy radical);
$R_1$ and $R_2$ representing hydrogen atoms.

According to a further preferred variant, namely when X represents a bond and Y represents a hydrogen atom whilst at least one of $R_1$ and $R_2$ represents a radical chosen from the alkyl, cycloalkyl or cycloalkylalkyl radicals, it is moreover preferable for the compounds of general formula (I) according to the invention to be such that they comprise at least one of the following characteristics:

at least one of $R_1$ and $R_2$ represents an alkyl radical comprising at least 4 carbon atoms whilst the other represents a hydrogen atom;
$R_1$ and $R_2$ both represent alkyl radicals comprising at least 3 carbon atoms each;
$R_1$ represents a cycloalkyl or cycloalkylalkyl radical and $R_2$ then preferably represents a hydrogen atom or a methyl radical (and more preferentially a hydrogen atom).

Generally, the compounds of general formula (I) are preferred, in which B represents a cycloalkyl radical (in particular the cyclopropyl radical), a carbocyclic aryl radical (in particular the phenyl radical), a heterocyclic aryl radical with 5 members containing from 1 to 2 hetero atoms chosen from O, S and N (in particular the thiophene, furane, pyrrole or thiazole radicals, and in particular the 2 thienyl radical) or also the NH—NO$_2$ radical. The compounds of general formula (I) are particularly preferred, in which B represents either a heterocyclic aryl radical with 5 members containing from 1 to 2 heteroatoms chosen from O, S and N (in particular the thiophene, furane, pyrrole or thiazole radicals, and in particular the 2 thienyl radical), or the NH—NO$_2$ radical. The compounds of general formula (I) are also more particularly preferred, in which B represents the 2 thienyl radical or the NH—NO$_2$ radical. The same preferences are applicable mutatis mutandis to B' when this radical is present in the compounds of general formula (I).

Also generally, when $R_4$ and $R_5$ form with the nitrogen atom which carries them a non-aromatic heterocycle with five to seven members containing from 1 to 2 heteroatoms, the elements for completing the heterocycle being chosen independently from a group comprising —CHR$_{10}$—, —NR$_{11}$—, —O— and —S—, the heterocycle formed (which is optionally substituted by the $R_{10}$ and $R_{11}$ radicals) is preferably chosen from the group comprising the pyrrolidine, piperidine, piperazine, morpholine, thiomorpholine, azepine and homopiperazine rings, and more preferentially from the group comprising the pyrrolidine, piperidine, piperazine, morpholine and thiomorpholine rings.

Moreover, $R_{13}$ preferably represents an alkyl radical or a haloalkyl radical.

Moreover, $R_{15}$ is preferably the phenyl radical, as is $R_{14}$.

In particular, the invention relates to the following compounds of general formula (I), described hereafter as examples (sometimes in the form of salts):

butyl-2-[4-(4-{[(1Z)-amino(thien-2-yl)methylene]-amino}phenyl)-1H-imidazol-2-yl]ethylcarbamate;
butyl-2-[4-(3-{[(1E)-amino(thien-2-yl)methylene]-amino}phenyl)-1H -imidazol-2-yl]ethylcarbamate;
butyl-2-[4-(4'-{[(1Z)-amino(thien-2-yl)methylene]amino}1,1'-biphenyl-4-yl)-1H-imidazol-2-yl]ethylcarbamate;
N'-(4-{2-[(cyclohexylamino)methyl]-1H-imidazol-4-yl}phenyl)thiophene-2-carboximidamide;
N'-(4-{2-[2-(cyclohexylamino)ethyl]-1H-imidazol-4-yl}phenyl)thiophene-2-carboximidamide;
N'-(3-{2-[(cyclohexylamino)methyl]-1H-imidazol-4-yl}phenyl)thiophene-2-carboximidamide;
N'-[4-(2-{[cyclohexyl(methyl)amino]methyl}-1H-imidazol-4-yl)phenyl]thiophene-2-carboximidamide;

N'-(4-{2-[(dibenzylamino)methyl]-1H-imidazol-4-yl}phenyl)thiophene-2-carboximidamide;
N'-(4-{2-[(benzylamino)methyl]-1H-imidazol-4-yl}phenyl)thiophene-2-carboximidamide;
N'-{-3-[2-(aminomethyl)-1H-imidazol-4-yl]phenyl}thiophene-2-carboximidamide;
N'-{-3-[2-({[(1E)-amino(thien-2-yl)methylene]-amino}methyl)-1H-imidazol-4-yl]phenyl}thiophene-2-carboximidamide;
N'-{4-[2-({[(1E)-amino(thien-2-yl)methylene]-amino}methyl)-1H-imidazol-4-yl]phenyl}thiophene-2-carboximidamide;
N-{3-[2-(2-cyclohexylethyl)-1H-imidazol-4-yl]phenyl}thiophene-2-carboximidamide;
N'-{3-[2-(1-pentylhexyl)-1H-imidazol-4-yl]phenyl}thiophene-2-carboximidamide;
N'-{4-[2-(2-cyclohexylethyl)-1H-imidazol-4-yl]phenyl}thiophene-2-carboximidamide;
N'-{3-[2-(cyclohexylmethyl)-1H-imidazol-4-yl]phenyl}thiophene-2-carboximidamide;
N'-{3-[2-(3-cyclohexylpropyl)-1H-imidazol-4-yl]phenyl}thiophene-2-carboximidamide;
N'-[3-(2-hexyl-1H-imidazol-4-yl)phenyl]thiophene-2-carboximidamide;
N-{4-[2-(2-cyclohexylethyl)-1H-imidazol-4-yl]phenyl}-N''-nitroguanidine;
N'-(4-{2-[(cycloheptylamino)methyl]-1H-imidazol-4-yl}phenyl)thiophene-2-carboximidamide;
N'-(4-{2-[(methylamino)methyl]-1H-imidazol-4-yl}phenyl)thiophene-2-carboximidamide:
N'-(4-{2-[(cyclobutylamino)methyl]-1H-imidazol-4-yl}phenyl)thiophene-2-carboximidamide:
N'-[4-(2-{[(2,2-diphenylethyl)amino]methyl}-1H-imidazol-4-yl)phenyl]thiophene-2-carboximidamide;
N'-{3-[2-(2-{[(1E)-amino(thien-2-yl)methylene]amino}ethyl)-1H-imidazol-4-yl]phenyl}thiophene-2-carboximidamide;
N'-(3-{2-[(phenylthio)methyl]-1H-imidazol-4-yl}phenyl)thiophene-2-carboximidamide;
N'-(4-{2-[(phenylthio)methyl]-1H-imidazol-4-yl}phenyl)thiophene-2-carboximidamide;
N'-{3-[2-(4-isobutylbenzyl)-1H-imidazol-4-yl]phenyl}thiophene-2-carboximidamide;

and the salts of the latter.

The invention also relates to, as medicaments, the compounds of general formula (I) as defined previously or the pharmaceutically acceptable salts of such compounds. It likewise relates to the pharmaceutical compositions containing, as active ingredient, the compounds of general formula (I) as defined previously or the pharmaceutically acceptable salts of such compounds, with a pharmaceutically acceptable excipient or excipients.

Moreover, a subject of the invention is also the use of compounds of general formula (I) as defined previously or of the pharmaceutically acceptable salts of such compounds for preparing a medicament intended to treat or prevent a disorder/disease chosen from the following disorders/diseases: pain, multiple sclerosis, disorders of the central or peripheral nervous system, cardiovascular disorders, disorders of the skeletal muscle and the neuromuscular joints, inflammatory diseases, hearing losses of traumatic, acoustic or toxic origin and tinnitus, complications linked with auto-immune and viral diseases and neurological diseases associated with intoxication, treatments or disorders of genetic origin. Preferably, the invention relates to the use of compounds of general formula (I) as defined previously or pharmaceutically acceptable salts of such compounds for preparing a medicament intended to treat a disorder/disease chosen from the following disorders/diseases: pain, disorders of the central or peripheral nervous system. More particularly, the invention relates to the use of compounds of general formula (I) as defined previously or pharmaceutically acceptable salts of such compounds for preparing a medicament intended to treat or prevent pain, in particular pain of neuropathic origin.

The invention also relates to the methods of treatment of the abovementioned diseases comprising the administration to the patient to be treated of a therapeutically effective dose of a compound of general formula (I).

For the medicaments, the pharmaceutical compositions, the uses for preparing the medicaments or the therapeutic uses, the preferences indicated for the compounds of general formula (I) are applied mutatis mutandis.

In certain cases, the compounds of general formula (I) according to the present invention can comprise asymmetrical carbon atoms. As a result, these compounds have two possible enantiomeric forms, i. e. the "R" and "S" configurations. The present invention includes the two enantiomeric forms of the compounds of general formula (I) and all combinations of these forms, including the "RS" racemic mixtures. In an effort to simplify matters, when no specific configuration is indicated in the structural formulae or the names of the compounds, it should be understood that the two enantiomeric forms and their mixtures are represented.

The pharmaceutical compositions containing a compound of the invention can be in solid form, for example powders, granules, tablets, gelatin capsules, liposomes, suppositories or patches. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or the glycols, similarly their mixtures, in varying proportions, in water.

The administration of a medicament according to the invention can be done by topical route, by oral route, by parenteral route, by intramuscular injection, by sub-cutaneous injection, by intra-venous injection, etc.

The dose of a product according to the present invention, to provide for treatment of the abovementioned diseases or disorders, varies depending on the administration method, the age and body weight of the subject to be treated, as well as the state of the latter, and will be finally decided by the attending doctor or vet. Such a quantity determined by the attending doctor or vet is here called "therapeutically effective quantity".

As an indication, the administration dose envisaged for a medicament according to the invention is comprised between 0.1 mg to 10 g depending on the type of active compound used.

In accordance with the invention, the compounds of general formula (I) can be prepared by the methods described below.

Preparation of the Compounds of the Invention

Preparation of the Compounds of General Formula (I):

The compounds of general formula (I) can be prepared for example from the intermediates of general formulae (I)$_P$, $(I)_{AP}$, $(I)_{AD}$, $(I)_D$, $(II)_1$, $(II)_{1A}$, $(III)_1$, $(III)_{1A}$, (IV), (IV'), (V), (VI), (VI'), (VII) and (VII') according to the procedures disclosed hereafter.

CASE no. 1: $R_3$ Represents a Hydrogen Atom:

Route no. 1:

Y represents H or an optionally substituted cycloalkyl or aryl radical, or also Y represents an $OR_{14}$, $Sr_{15}$ or $NR_4R_5$ radical in which $R_4$ represents —$C(O)R_9$, —$C(O)OR_9$, —$C(O)NHR_9$ or —$SO_2R_9$, or in which $R_4$ represents an optionally substituted alkyl, cycloalkyl, cycloalkylaklyl or bis-phenylaklyl or aryl or aralkyl radical and $R_5$ does not represent H, or also in which $R_4$ and $R_5$ form with the nitrogen atom which carries them a heterocycle:

When Y represents a hydrogen atom, a cycloalkyl radical, an optionally substituted aryl radical or an $OR_{14}$, $SR_{15}$ or $NR_4R_5$ radical in which $R_4$ represents a —$C(O)R_9$, —$C(O)OR_9$, —$C(O)NHR_9$ or —$SO_2R_9$ radical, or in which $R_4$ represents an alkyl, cycloalkyl, cycloalkylalkyl or bis-phenylalkyl radical or an aryl or aralkyl radical optionally substituted on the aromatic ring and $R_5$ does not represent a hydrogen atom or also in which $R_4$ and $R_5$ form with the nitrogen atom which carries them an optionally substituted heterocycle, the corresponding compounds of general formula (I), hereafter called compounds of general formula $(I)_1$, can be prepared, Diagram 1, from the intermediates of general formula $(II)_1$ in which X, $R_1$, $R_2$ and A have the same meaning as in general formula (I), W represents an $NO_2$ or $N_3$ group and Y represents a hydrogen atom, a cycloalkyl radical or an $NR_4R_5$ radical in which $R_4$ and $R_5$ have the same meanings as above. Said intermediates of general formula $(II)_1$ are subjected, in a protic polar solvent such as ethanol (optionally in a mixture with dichloromethane), to hydrogenation catalyzed by palladium on carbon (or any other appropriate reaction) in order to produce the intermediates of general formula $(III)_1$. The compounds of general formula $(I)_1$ are then obtained by reaction, in a solvent such as isopropanol, of the intermediates of general formula $(III)_1$ either with one of the compounds of general formulae (IV), (V), (VI) or (VII) (deprotection in acid medium of the compound obtained in intermediate fashion also being necessary in the case of the reaction with the compound of general formula (VII)), or with benzoylisothiocyanate followed by a halogenoalkyl of general formula $R_8$-Hal.

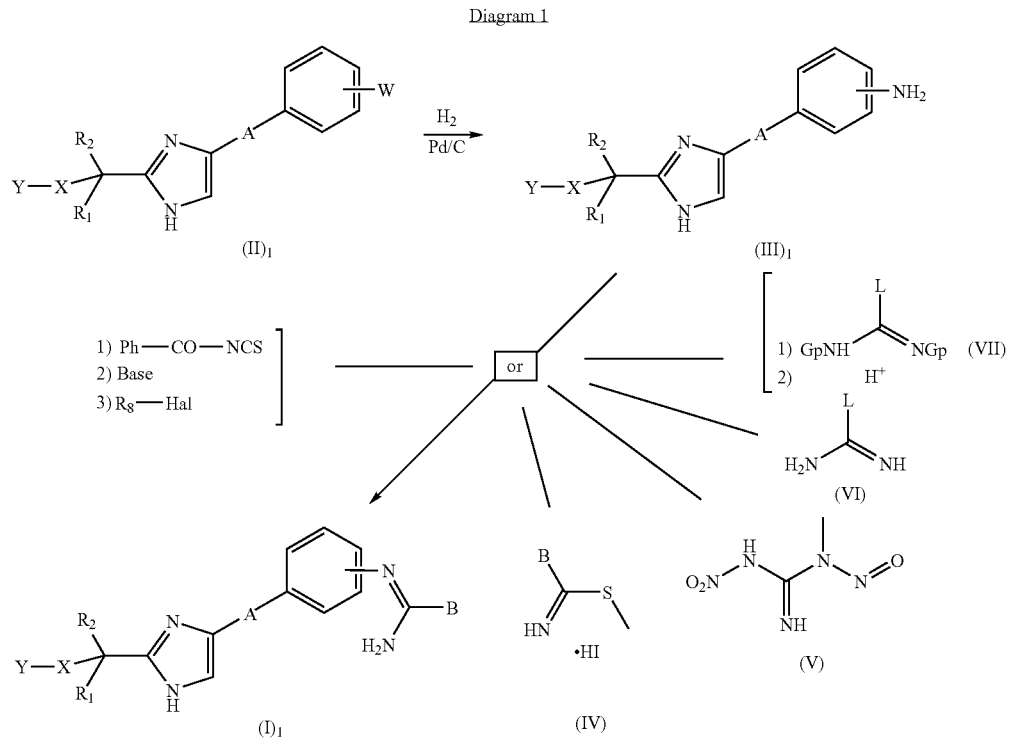

Diagram 1

Thus, in the particular case where B represents an alkyl radical, a cycloalkyl radical, an $NR_6R_7$ radical in which $R_6$ and $R_7$ form with the nitrogen atom which carries them a non-aromatic heterocycle with five to six members, a carbocyclic aryl radical or a heterocyclic aryl radical, the conversion of the compound of general formula $(III)_1$ with the compound of general formula (IV) can be carried out as represented in Diagram 1.

In the particular case where B represents $NHNO_2$, the compound of general formula $(III)_1$ is condensed with the compound of formula (V) as represented in Diagram1.

In the particular case where B represents an $NR_6R_7$ radical in which $R_6$ represents a hydrogen atom or an alkyl, alkenyl or alkynyl radical and $R_7$ represents a hydrogen atom or an alkyl radical, the compound of general formula $(III)_1$ can be condensed with the compound of general formula (VI) in which L represents, for example, a pyrazole ring or also with the compound of general formula (VII) in which, for example L represents a pyrazole ring and Gp the Boc group (*Tetrahedron Lett.* (1993) 34 (21), 3389–3392) or L represents the —N—$SO_2$—$CF_3$ group and Gp the Boc group (*J. Org. Chem.* (1998) 63, 3804–3805). In the case where a compound of general formula (VII) is used, the deprotection of the guanidine function is then carried out, for example, in the presence of a strong acid such as for example trifluoroacetic acid, in order to lead to the compound of general formula $(I)_1$.

Finally, in the particular case where B represents an $SR_8$ radical, the thioureas of general formula $(I)_1$ can be prepared in 3 stages. The reaction of the benzoylisothiocyanate on the aniline of general formula $(III)_1$ in a solvent such as, for example, acetone, leads to the intermediate benzoyl-thiourea which is then hydrolyzed in a standard fashion by heating in basic medium. The thiourea thus obtained is then alkylated, using, for example, a halogenated derivative of general formula $R_8$-Hal, by heating in an inert solvent, in order to produce the compound of general formula $(I)_1$.

Route no. 2:

Y represents H or a optionally substituted cycloalkyl or aryl radical or also an $NR_4R_5$ radical in which $R_4$ does not represent —$C(O)R_9$, —$C(O)OR_9$, —$C(O)NHR_9$ or —$SO_2R_9$, or in which $R_4$ represents an alkyl, cycloalkyl, cycloalkylalkyl or bis-phenylalkyl radical or also optionally substituted aryl or aralkyl and $R_5$ represents H:

When Y represents an $NR_4R_5$ radical in which $R_4$ does not represent a —$C(O)R_9$, —$C(O)OR_9$, —$C(O)NHR_9$ or —$SO_2R_9$ radical or an optionally substituted aryl radical, or in which $R_4$ represents an alkyl, cycloalkyl, cycloalkylalkyl or bis-phenylalkyl radical or an aryl or aralkyl radical optionally substituted on the aromatic ring and $R_5$ represents a hydrogen atom, the corresponding compounds of general formula (I), hereafter called compounds of general formula $(I)_2$ can be prepared, Diagram 2, from the compounds of general formula $(I)_P$ in which $X$, $R_1$, $R_2$, $R_5$, A and B have the same meaning as in general formula (I) and Gp represents a standard amine protective group (such as a tert-butoxycarbonyl group). Said compounds of general formula $(I)_P$ are deprotected in order to produce the compounds of general formula $(I)_D$, the reaction being carried out under standard conditions for a person skilled in the art (cf. *Protective groups in organic synthesis*, 2nd ed., (John Wiley & Sons Inc., 1991)); this deprotection is thus carried out for example in an acid medium (in particular using hydrochloric acid; the reaction can be carried out in a solvent such as ethyl acetate). The compounds of general formula $(I)_D$ are then alkylated according to techniques known to a person skilled in the art in order to produce the compounds of general formula $(I)_2$; for example, in the case where $R_4$ represents an alkyl or cycloalkylalkyl radical, the compounds of general formula $(I)_D$ are reacted with halides of general formula $R_4$Hal in which Hal is a halogen atom, or also, in the case where $R_4$ represents a cycloalkyl radical or a radical of general formula R—$CH_2$— in which R represents an alkyl, aralkyl or bis-phenylalkyl radical, a condensation reaction of the compounds of general formula $(I)_D$ is carried out with the appropriate ketones or the aldehyde of general formula R—CHO in the presence of a reducing agent such as sodium triacetoxyborohydride or sodium borohydride in a lower aliphatic alcohol such as methanol and optionally in the presence of molecular sieves, this reaction being preferably carried out at ambient temperature.

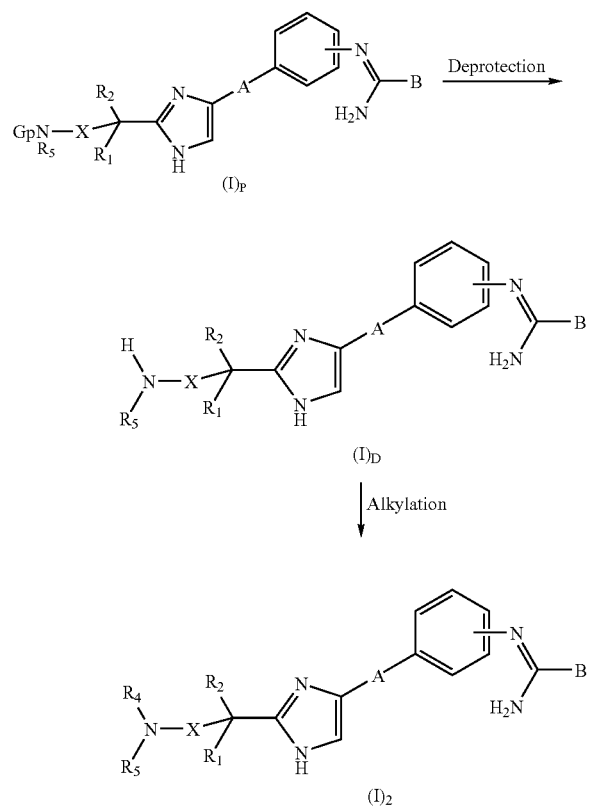

Diagram 2

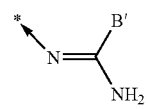

Route no. 3:

Y represents an amidine-type radical:

When Y represents a type radical, the corresponding compounds of general formula (I), hereafter called compounds of general formula $(I)_3$, can be prepared, Diagram 3, from the compounds of general formula $(I)_1$ in which Y represents an $NH_2$ radical. The compounds of general formula $(I)_2$ are then obtained by reaction, in a solvent such as isopropanol, of the compounds of general formula $(I)_1$ in which X, $R_1$, $R_2$, A and B have the same meaning as in general formula (I) and Y represents an $NH_2$ radical either with one of the compounds of general formulae (IV'), (V), (VI') or (VII') (deprotection in an acid medium of the compound obtained in intermediate fashion also being necessary in the case of reaction with the compound of general formula (VII')), or with benzoylisothiocyanate followed by a halogenoalkyl of general formula $R_8$-Hal (cf. CASE no. 1, route no. 1).

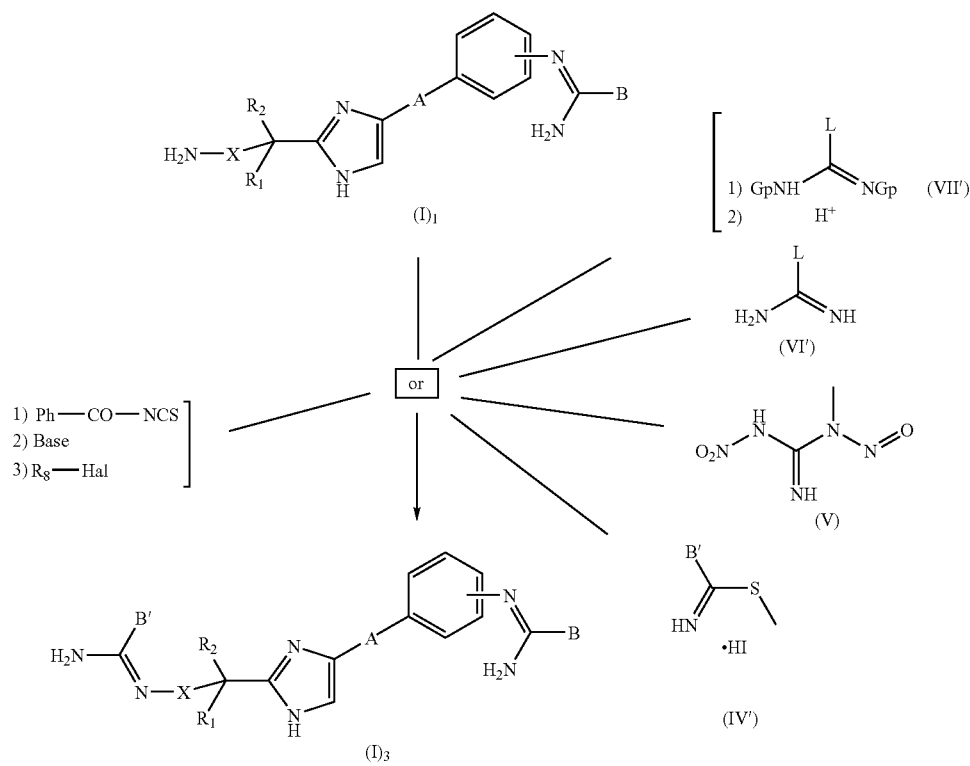

Diagram 3

CASE no. 2: $R_3$ does not Represent a Hydrogen Atom:

Route no. 1:

Y represents H or an optionally substituted cycloalkyl or aryl radical, or also Y represents an $OR_{14}$, $Sr_{15}$ or $NR_4R_5$ radical in which $R_4$ represents $—C(O)R_9$, $—C(O)OR_9$, $—C(O)NHR_9$ or $—SO_2R_9$, or in which $R_4$ represents an alkyl, cycloalkyl, cycloalkylalkyl or bis-phenylalkyl radical or an optionally substituted aryl or aralkyl radical and $R_5$ does not represent H, or also in which $R_4$ and $R_5$ form, with then nitrogen atom which carries them, a heterocycle:

When $R_3$ represents an alkyl or aralkyl radical and Y represents a hydrogen atom, a cycloalkyl radical, an optionally substituted aryl radical or an $OR_{14}$, $SR_{15}$ or $NR_4R_5$ radical in which $R_4$ represents a $—C(O)R_9$, $—C(O)OR_9$, $—C(O)NHR_9$ or $—SO_2R_9$ radical, or in which $R_4$ represents an alkyl, cycloalkyl, cycloalkylalkyl or bis-phenylalkyl radical or an aryl or aralkyl radical optionally substituted on the aromatic ring and $R_5$ does not represent a hydrogen atom or also in which $R_4$ and $R_5$ form with the nitrogen atom which carries them an optionally substituted heterocycle, a stage can simply be added to synthesis route no. 1 of CASE 1. The nitrogen atom in position 1 of the imidazole ring is alkylated before carrying out catalyzed hydrogenation, then the usual stages of route no. 1 of CASE no. 1 are used in order to produce the compounds of general formula $(I)_{1,4}$, in other words the compounds of general formula $(I)_1$ in which $R_3$ represents an alkyl or aralkyl radical and X, Y, $R_1$, $R_2$, A and B have the same meanings as in general formula $(I)_1$. This synthesis method is summarized in Diagram 1a hereafter.

The compounds of general formula $(I)_{1,4}$, can be prepared, Diagram 1a, from the intermediates of general formula $(II)_1$ in which X, $R_1$, $R_2$ and A have the same meaning as in general formula (I), W represents an $NO_2$ or $N_3$ group, Y represents a hydrogen atom, a cycloalkyl radical, an optionally substituted aryl radical, an $OR_{14}$ or $SR_{15}$ radical, or an $NR_4R_5$ radical in which $R_4$ represents a $—C(O)R_9$, $—C(O)OR_9$, $—C(O)NHR_9$, $—SO_2R_9$ or optionally substituted aryl radical, or in which $R_4$ represents an alkyl, cycloalkyl, cycloalkylalkyl or bis-phenylalkyl radical or also an optionally substituted aralkyl radical and $R_5$ does not represent a hydrogen atom. Said intermediates of general formula $(II)_1$ are first alkylated according to techniques known to a person skilled in the art, for example by means of a halogenated derivative of general formula $R_3Hal$ in which Hal is a halogen atom. The intermediates of general formula $(II)_{1,4}$ are then subjected, in a protic polar solvent such as ethanol (optionally in a mixture with dichloromethane), to hydrogenation catalyzed by palladium on carbon in order to produce the intermediates of general formula $(III)_{1,4}$. The compounds of general formula $(I)_{1,4}$ are then obtained by reaction, in a solvent such as isopropanol, of the intermediates of general formula $(III)_{1,4}$ either with the compounds of general formulae (IV), (V), (VI) or (VII) (deprotection in an acid medium of the compound obtained in intermediate fashion also being necessary in the case of the reaction with the compound of general formula (VII)), or with benzoylisothiocyanate then a halogenoalkyl of general formula $R_8$-Hal (cf. CASE no. 1, route no. 1).

Diagram 1a

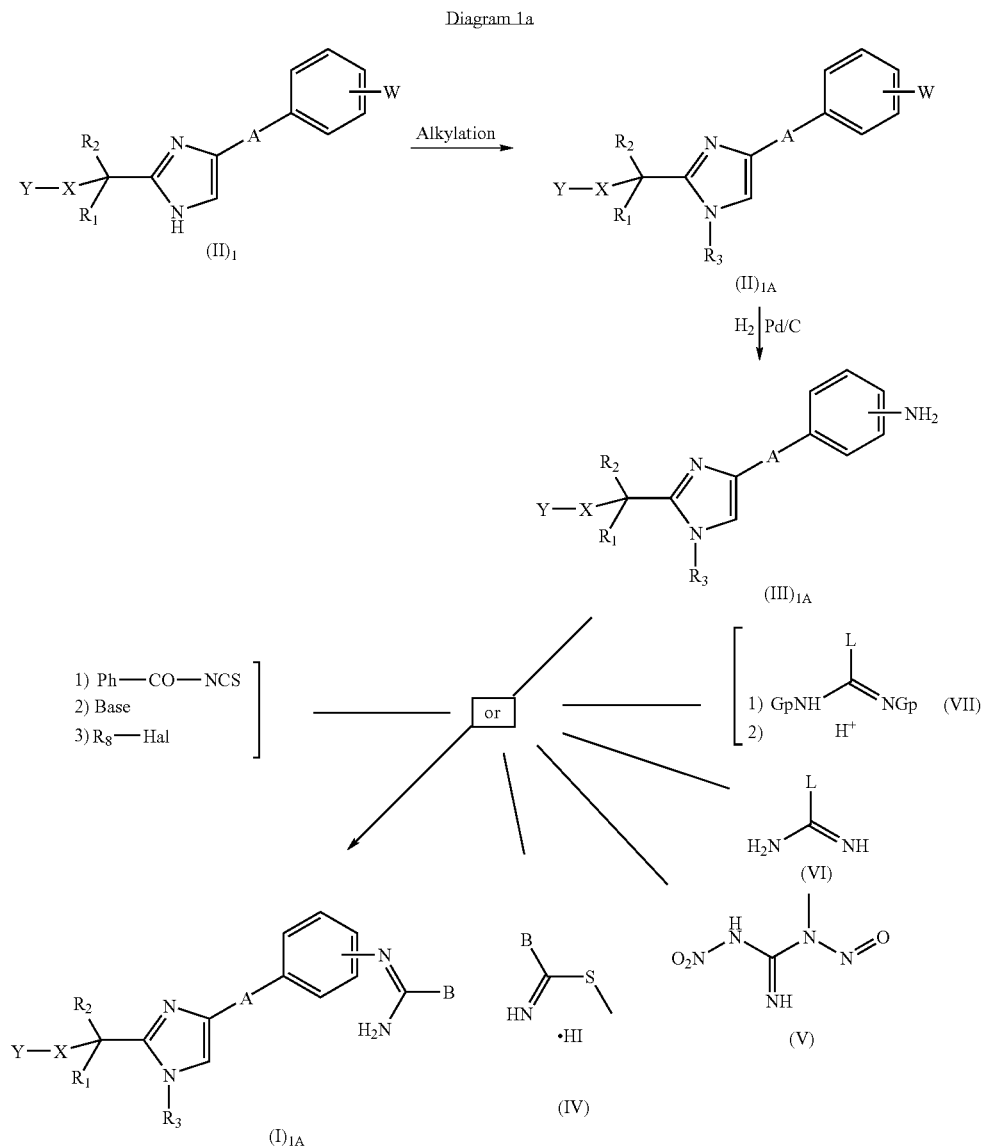

Route no. 2:

Y represents H or a cycloalkyl or optionally substituted aryl radical or also an $NR_4R_5$ radical in which $R_4$ does not represent —$C(O)R_9$, —$C(O)OR_9$, —$C(O)NHR_9$ or —$SO_2R_9$, or in which $R_4$ represents an alkyl, cycloalkyl, cycloalkylalkyl or bis-phenylalkyl radical or also an optionally substituted aryl or aralkyl radical, and $R_5$ represents H:

When $R_3$ represents an alkyl or aralkyl radical and Y represents an $NR_4R_5$ radical in which $R_4$ does not represent a —$C(O)R_9$, —$C(O)OR_9$, —$C(O)NHR_9$ or —$SO_2R_9$ radical, or in which $R_4$ represents an alkyl, cycloalkyl, cycloalkylalkyl or bis-phenylalkyl radical or an aryl or aralkyl radical optionally substituted on the aromatic ring and $R_5$ represents a hydrogen atom, a stage can simply be added to synthesis route no. 2 of CASE no. 1. The nitrogen atom in position 1 of the imidazole ring is alkylated whilst the amine function of the side chain in position 2 of the imidazole ring is protected, then the usual stages of route no. 2 of CASE no. 1 are used in order to produce the compounds of general formula $(I)_{2A}$, in other words the compounds of general formula $(I)_2$ in which $R_3$ represents an alkyl or aralkyl radical and A, B, X, $R_1$, $R_2$, $R_4$ and $R_5$ have the same meanings as in general formula $(I)_2$. This synthesis method is summarized in Diagram 2a hereafter.

The compounds of general formula $(I)_P$ are first alkylated according to techniques known to a person skilled in the art, for example by means of a halogenated derivative of general formula $R_3$Hal in which Hal is a halogen atom. The compounds of general formula $(I)_{AP}$ obtained are then deprotected in order to produce the compounds of general formula $(I)_{AD}$, the reaction being carried out under standard conditions for a person skilled in the art (cf. *Protective groups in organic synthesis,* 2nd ed., (John Wiley & Sons Inc., 1991)); this deprotection is thus carried out for example in an acid medium (in particular using hydrochloric acid; the reaction can be carried out in a solvent such as ethyl acetate). The compounds of general formula $(I)_{AD}$ are then alkylated according to techniques known to a person skilled in the art in order to produce the compounds of general formula (I)$_{2,4}$; for example, in the case where R$_4$ represents an alkyl or cycloalkylalkyl radical, the compounds of general formula (I)$_{AD}$ are reacted with halides of general formula R$_4$Hal in which Hal is a halogen atom, or also, in the case where R$_4$ represents a cycloalkyl radical or a radical of general formula R—CH$_2$— in which R represents an alkyl, aralkyl or bis-phenylalkyl radical, a condensation reaction of the compounds of general formula (I)$_{AD}$ is carried out with the appropriate cycloalkylketones or the aldehyde of general formula R—CHO in the presence of a reducing agent such as sodium triacetoxyborohydride or sodium borohydride in a lower aliphatic alcohol such as methanol and optionally in the presence of molecular sieves, this reaction preferably being carried out at ambient temperature.

Diagram 2a

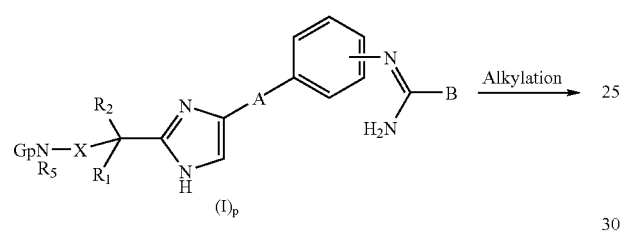

(I)$_P$

↓ Alkylation

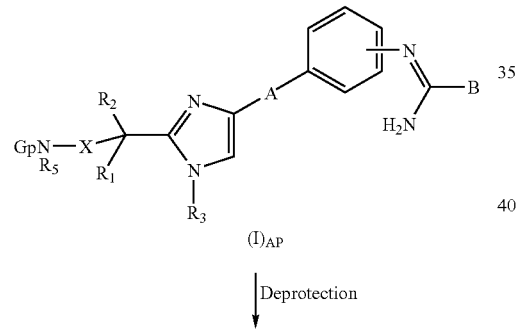

(I)$_{AP}$

↓ Deprotection

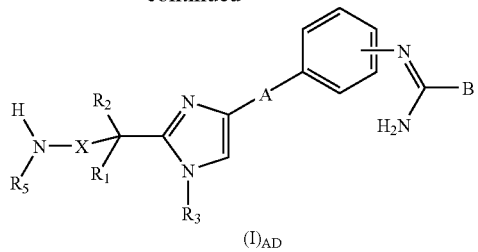

(I)$_{AD}$

↓ Alkylation

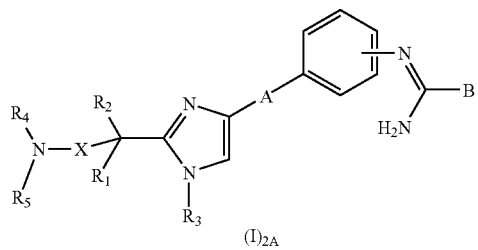

(I)$_{2A}$

Route no. 3:

Y represents an amidine-type radical:
When Y represents a

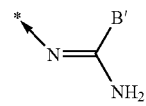

type radical and R$_3$ represents an alkyl or aralkyl radical, the corresponding compounds of general formula (I), hereafter called compounds of general formula (I)$_{3,4}$, can be prepared according to a method analogous to that described in synthesis route no. 3 of CASE no. 1, the compound of general formula (I)$_1$ in which Y represents NH$_2$ and R$_3$ represents a hydrogen atom simply being replaced by the compound of general formula (I)$_{1,4}$ in which Y represents NH$_2$ and R$_3$ represents an alkyl or aralkyl radical. This synthesis method is summarized in Diagram 3a hereafter.

Diagram 3a

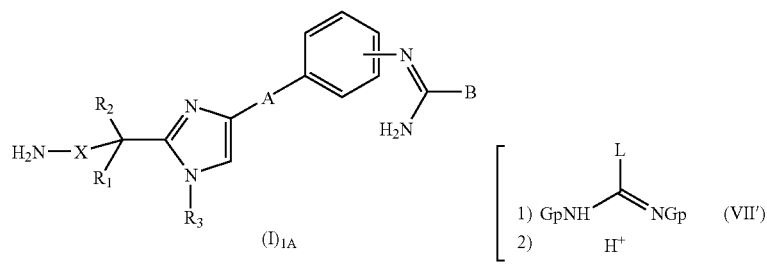

(I)$_{1A}$

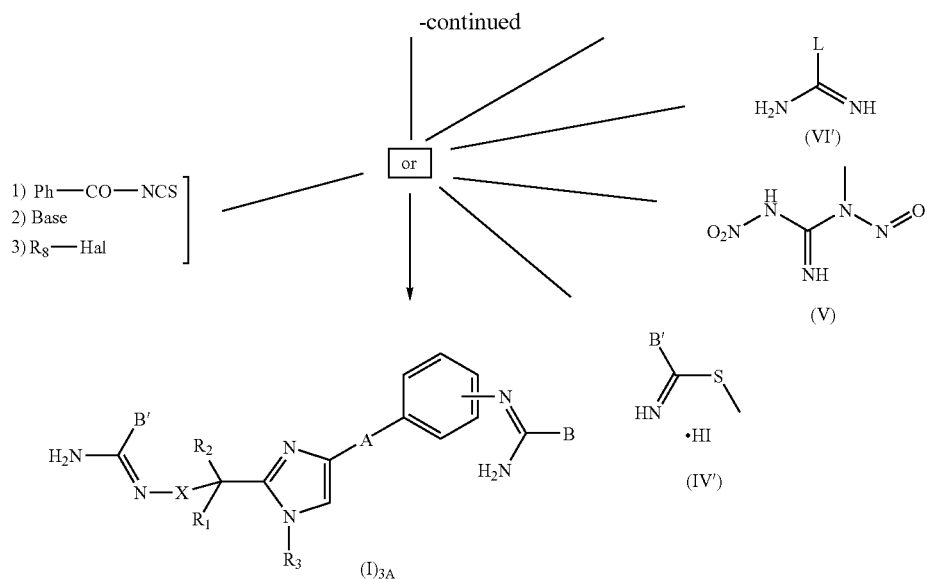

Preparation of Certain Non-Commercial Synthesis Intermediates:

Preparation of the Compounds of General Formula (I)$_P$

These compounds are in fact also compounds of general formula (I) in which Y represents an NR$_4$R$_5$ group in which R$_4$ represents a particular alkoxycarbonyl group (such as a tert-butoxycarbonyl group). They can therefore be prepared according to the procedure described for the compounds of general formula (I) above (cf. route 1).

Preparation of the Compounds of General Formula (II)$_1$

The compounds of general formula (II)$_1$ are obtained by cyclocondensation reaction of the acid of general formula (VIII)$_1$ with the α-halogenoketone of general formula (IX)$_1$. For example, Diagram 4, caesium carbonate is added to the acid of general formula (VIII)$_1$. The intermediate obtained is condensed with an α-halogenoketone of general formula (IX)$_1$ then a large excess of ammonium acetate (for example 15 or 20 equivalents per equivalent of acid of general formula (VIII)$_1$) is added. This reaction is preferably carried out in a mixture of xylenes and while heating (if appropriate, the water formed during the reaction can also be eliminated simultaneously).

Diagram 4

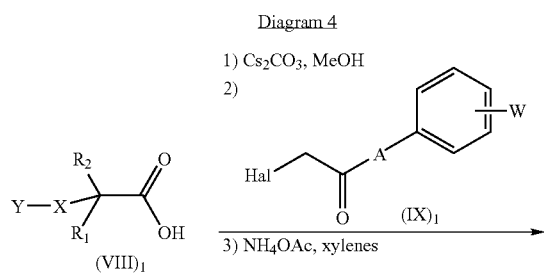

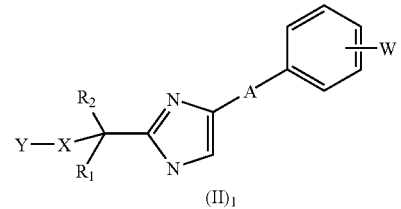

Preparation of the Compounds of General Formula (IV) or (IV')

The compounds of general formula (IV) in which B represents an alkyl radical, a carbocyclic aryl radical or a heterocyclic aryl radical can be obtained, for example, Diagram 5, by reaction of the thioamides of general formula (IV).1 with methyl iodide in a solvent such as acetone. The synthesis is identical for the compounds of general formula (IV') ((IV').1 and B' replacing (IV).1 and B respectively in Diagram 5)

Diagram 5

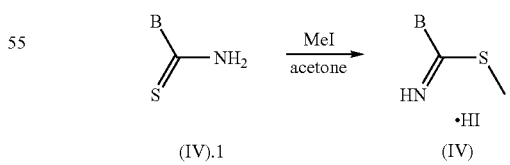

Preparation of the Compound of Formula (V)

The preparation of these compounds can be carried out according to methods known to a person skilled in the art such as for example that described in the following publication: *J. Amer. Chem. Soc.* (1947), 69, 3028–3030).

Preparation of Certain Compounds of General Formula (VIII)$_1$

The compounds of general formula (VIII)$_1$ in which $R_4$ represents a —C(O)OR$_9$ radical and X, $R_1$, $R_2$, $R_5$ and $R_9$ have the same meaning as in general formula (I) are prepared, Diagram 6, by reaction, under basic conditions (created for example by the addition of sodium hydroxide and water or in the presence of an organic base such as triethylamine), of the amino acid of general formula (X)$_1$ with the halogenated derivative of general formula $R_9$—OC(O)—Hal in which Hal represents a halogen atom. Once the reaction is terminated, the medium is acidified (for example by the addition of hydrochloric acid) in order to produce the amino acid of general formula (VIII)$_1$.

Diagram 6

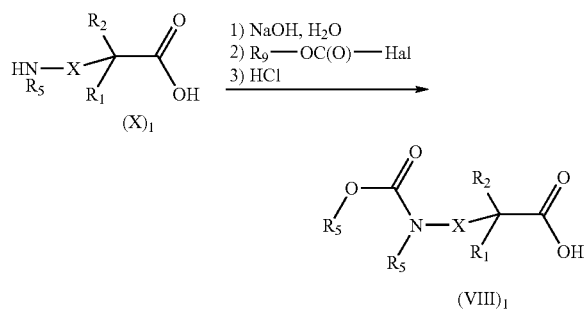

The compounds of general formula (VIII)$_1$ in which $R_4$ represents a —C(O)R$_9$ radical and X, $R_1$, $R_2$ and $R_5$ have the same meaning as in general formula (I) are prepared, Diagram 7, by condensation of the amino acids of general formula (X)$_1$ with carboxylic acids (or the corresponding acid chlorides) of general formula $R_9$—COOH under standard peptide synthesis conditions (M. Bodanszky and A. Bodanszky, *The Practice of Peptide Synthesis*, 145 (Springer-Verlag, 1984)) in a polar solvent such as tetrahydrofuran, dichloromethane or dimethylformamide in the presence of a coupling reagent such as dicyclohexylcarbodiimide (DCC), 1,1'-carbonyldiimidazole (CDI) (*J. Med. Chem.* (1992), 35(23), 4464–4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)).

Diagram 7

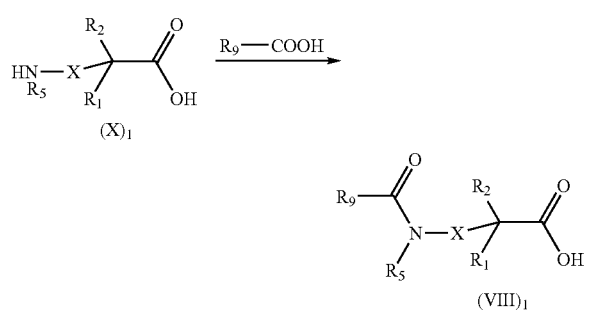

The compounds of general formula (VIII)$_1$ in which $R_4$ represents a —C(O)NHR$_9$ radical and X, $R_1$, $R_2$ and $R_5$ have the same meaning as in general formula (I) are prepared, Diagram 8, by reaction of the amino acids of general formula (X)$_1$ with the isocyanates of general formula $R_9$—NCO; the reaction can be carried out at ambient temperature in a solvent such as chloroform.

Diagram 8

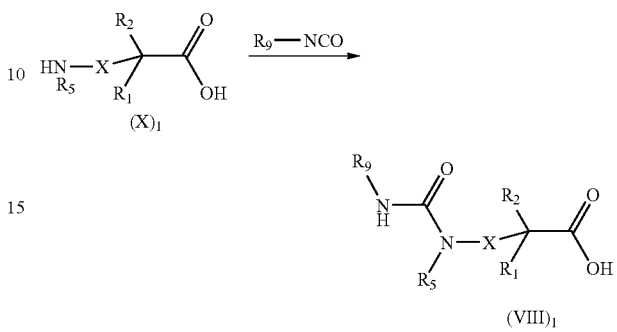

The compounds of general formula (VIII)$_1$ in which $R_4$ represents a —C(O)NHR$_9$ radical and X, $R_1$, $R_2$ and $R_5$ have the same meaning as in general formula (I) are prepared, Diagram 9, by reaction of the amino acids of general formula (X), with the sulphochlorides of general formula $R_9$-SO$_2$Cl under standard conditions; the reaction can for example be carried out at ambient temperature in a solvent such as dimethylformamide in the presence of a base such as triethylamine.

Diagram 9

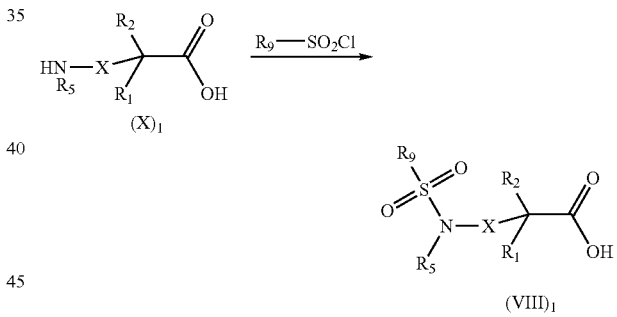

Preparation of the Compounds of General Formula (IX)$_1$

The compounds of general formula (IX)$_1$, in which Hal represents a halogen atom (for example a chlorine or bromine atom), W represents an NO$_2$ or N$_3$ group and A has the same meaning as in general formula (I), are prepared, Diagram 10, by reaction of the ketone of general formula (XI)$_1$ with a halogenating agent. For example, in the particular case of bromination, the reaction can be carried out with a bromination agent such as CuBr$_2$ (*J. Org. Chem.* (1964), 29, 3459), bromine (*J. Het. Chem.* (1988), 25, 337), N-bromosuccinimide (*J. Amer. Chem. Soc.* (1980), 102, 2838) in the presence of acetic acid in a solvent such as ethyl acetate or dichloromethane, HBr or Br$_2$ in ether, ethanol or acetic acid (*Biorg. Med. Chem. Lett.* (1996), 6(3), 253–258; *J. Med. Chem.* (1988), 31(10), 1910–1918; *J. Am. Chem. Soc.* (1999), 121, 24) or also using a bromination resin (*J. Macromol. Sci. Chem.* (1977), A11, (3) 507–514).

Diagram 10

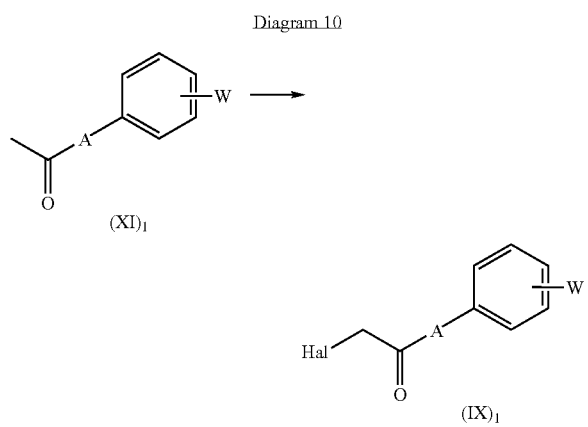

Preparation of the other Intermediates

The preparation of the other non-commercial intermediates is described in the literature or is within the scope of a person skilled in the art by means of standard synthesis methods.

Unless otherwise specified, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no event be considered as a limit to the scope of the invention.

EXAMPLES

Method used for Measurement of the Retention Time (r.t.) and of the Molecular Peak (MH+)

The compounds are characterized by their retention time (r.t.), expressed in minutes, determined by liquid chromatography (LC), and their molecular peak (MH+) determined by mass spectrometry (MS), a single quadrupole mass spectrometer (Micromass, Platform model) provided with an electrospray source is used with a resolution of 0.8 da at 50% valley.

In the examples below, the elution conditions corresponding to the results shown are as follows: passage from an acetonitrile-water-trifluoroacetic acid mixture 50-950-0.2 (A) to an acetonitrile-water mixture 950-50 (B) through a linear gradient over a period of 8.5 minutes, then elution with the pure mixture B for 10.5 minutes. cl Example 1 butyl-2-[4-(4-{[(1Z)-amino(thien-2-yl)methylene]-amino}phenyl)-1H-imidazol-2-yl]ethylcarbamate hydrochloride 1.1) butyl-2-[4-(4-azidophenyl)-1H-imidazol-2-yl]ethylcarbamate A mixture containing N-(butoxycarbonyl)-β-alanine (3 g; 15.1 mmol) and caesium carbonate (2.43 g; 7.55 mmol) in 50 ml of anhydrous methanol is stirred for one hour. This mixture is evaporated to dryness then diluted with 60 ml of dimethylformamide. 4-azidophenacyl bromide is added (3.64 g; 15.1 mmol) then the resultant mixture is stirred for 2 hours. The solvent is evaporated off using a vane pump. 80 ml of ethyl acetate is added and the caesium bromide is filtered on frit. After evaporation of the filtrate, 200 ml of xylenes is added. Ammonium acetate (23 g; 0.3 mol) is then added and the mixture heated to reflux for 1 hour 30 minutes before being poured into iced water to which 80 ml of ethyl acetate is added. After decantation, the organic phase is washed with a saturated solution of sodium chloride. The organic phase is then dried over magnesium sulphate and the solvent evaporated off. The oil obtained is purified on a silica column (eluent: ethyl acetate-heptane/8-2). The expected product is recovered in the form of a black oil with a yield of 65%.

1.2) 2-[4-(4-aminophenyl)-1H-imidazol-2-yl]ethyl-carbamate

Intermediate 1.1 (3 g; 9.15 mmol) is dissolved in 50 ml of ethanol in the presence of palladium on carbon (approximately 10% by mass). This mixture is hydrogenated under two bar for 18 hours. The reaction mixture is then filtered on a Millipore® filter then rinsed in ethanol. After evaporation of the solvent, a light brown coloured foam is obtained with a yield of 88%.

NMR $^1$H (δ ppm, DMSO): 0.84 (t, 3H); 1.27–1.29(m, 2H); 1.45–1.48 (m, 2H); 3.05 (m, 2H); 3.42 (m, 2H); 3.90 (m, 2H); 5.5–6.2 (broad m, 1H); 6.67–6.69 (d 7.34 (broad s, 1H); 7.47–7.49 (d, 2H); 7.70 (s, 1H); 14.33 (broad s, 2H). MH+=303. 2.

1.3) Methyl thiophene-2-carbimidothioate

Methyl iodide (66 g; 0.46 mol) is added drop wise at 0° C. to a solution of thiophene-2-carbothioamide (50 g; 0.33 mol) in 500 ml of acetone. After the addition, stirring is maintained for two hours at 23° C. The precipitate formed is filtered on frit and washed twice with 100 ml of acetone before being dried under vacuum (in a bell jar). A yellow powder is obtained with a yield of 97%.

NMR $^1$H (δ ppm, DMSO): 2.8 (s, 3H); 7.42 (m, 1H); 8.125 (d, 1H); 8.27 (d, 1H); 10–12 (broad m, 1H).

1.4) Butyl-2-[4-(4-{[(1Z)-amino(thien-2-yl)methylene]amino}phenyl)-1H-imidazol-2-yl]ethylcarbamate Intermediate 1.2 (2.5 g; 8.2 mmol) is suspended in 30 ml of 2 propanol in the presence of intermediate 1.3 (1.2 eq.). The reaction mixture is maintained at 50° C. for 18 hours before being concentrated to dryness. The residue is taken up in 50 ml of ethyl acetate and 50 ml of a saturated solution of sodium carbonate. The mixture is stirred for 30 minutes before being decanted. The organic phase is then washed with a saturated solution of sodium chloride then dried over sodium sulphate. The solvents are evaporated off and the foam obtained is purified on a silica column (eluent: $CH_2Cl_2$-MeOH/97-3 to 90-10). A light yellow coloured powder is obtained with a yield of 57%. Melting point: 146.2° C.

MH+=412.2.

1.5) Butyl-2-[4-(4-{[(1Z)-amino(thien-2-yl)methylene]amino}phenyl)-1H-imidazol-2-yl]ethylcarbamate hydrochloride Intermediate 1.4 (1 g; 2.43 mmol) is dissolved in ethanol (20 ml). 1 N hydrochloric acid in solution in ether (9.7 ml;

9.7 mmol). The mixture is stirred for one hour. After concentration to dryness, the residue is taken up in ether (15 ml) and the mixture is stirred for 15 minutes. After filtration on frit and washing with ether of the solid recovered, the latter is dried under vacuum (bell jar). The expected product is obtained in the form of a cream coloured solid with a yield of 100%.

Melting point: >260° C. MH+=412.2.

The compounds of examples 2 and 3 are prepared according to an operating method analogous to that described for the compound of Example 1.

Example 2 butyl-2[4(3-{[(1E)-amino(thien-2yl)methylene]-amino}phenyl)-1H-imidazol-2-yl]ethylcarbamate hydrochloride Melting point: 210–212° C. MH+=412.2

Example 3 butyl 2-[4-(4'-{[(1Z)-amino(thien-2-yl)methylene]amino}-1,1'-biphenyl-4-yl-1H-imidazol-2-yl]ethylcarbamate hydrochloride Melting point: 97–98° C. MH+=488.2.

Example 4

N'-(4-{2-[(cyclohexylamino)methyl]-1H-imidazol-4-yl}phenyl)thiophene-2-carboximidamide hydrochloride

4.1) Tert-butyl [4-(4-azidophenyl)-1H-imidazol-2-yl]methylcarbamate

A mixture containing N-(tert-butoxycarbonyl)-glycine (5 g; 28.5 mmol) and caesium carbonate (4.6 g; 14.2 mmol) in 30 ml of anhydrous methanol is stirred for one hour. This mixture is evaporated to dryness then diluted with 60 ml of dimethylformamide. 4-azidophenacyl bromide (6.84 g; 28.5 mmol) is added, then the resultant mixture is stirred for 2 hours. The solvent is evaporated off using a vane pump. 80 ml of ethyl acetate is added and the caesium bromide is filtered on frit. After evaporation of the filtrate, 200 ml of xylenes is added, then ammonium acetate (44 g; 0.57 mol), and the mixture is heated to reflux for 1 hour 30 minutes before being poured into iced water to which 80 ml of ethyl acetate have been added. After decantation, the organic phase is neutralized with a saturated solution of sodium bicarbonate followed by filtration on a glass microfibre filter (GF/A, Whatman). The organic phase is washed with a saturated solution of sodium chloride then dried over sodium sulphate and the solvent evaporated off. The black oil obtained is purified on a silica column (eluent: ethyl acetate-heptane/6-4 to 3-7). A brown coloured powder is obtained which, after washing with isopropyl ether, leads to a light brown-coloured powder with a yield of 48%.

NMR $^1$H (δ ppm, DMSO): 1.39 (s, 9H); 4.16 (m, 2H); 7.06 (d, 2H); 7.24 (broad s, 1H); 7.48 (s, 1H); 7.77 (d, 2H); 11.8 (broad s, 1H).

4.2) Tert-butyl [4-(4-aminophenyl)-1H-imidazol-2-yl]methylcarbamate

Intermediate 4.1 (4.3 g; 13.6 mmol) is dissolved in 50 ml of an ethanol-$CH_2Cl_2$ mixture 2-1 in the presence of palladium on carbon (approximately 10% by mass). This mixture is hydrogenated under a pressure of 2 bar of hydrogen for 24 hours. The reaction mixture is then filtered on a glass micro fibre filter (GF/A, Whatman) then rinsed in ethanol. After evaporation of the solvent, the residue is stirred in ether. The mixture is then filtered on frit, then washed in ether and isopentane. A pale yellow coloured powder is obtained with a yield of 100%.

NMR $^1$H (δ ppm, DMSO): 1.39 (s, 9H); 4.17 (m, 2H); 6.54 (d, 2H); 7.16–7.19 (broad s, 2H); 7.35 (d, 2H).

4.3) Tert-butyl [4-(4-{[(1E)-amino(thien-2-yl)methylene]amino}phenyl)-1H-imidazol-2-yl]methylcarbamate Intermediate 4.2 (3.9 g; 13.6 mol) is suspended in 30 ml of propanol-2 in the presence of intermediate 1.3. The mixture is heated to a temperature of 60° C. for 48 hours. After concentration to dryness of the mixture, the residue is taken up in 50 ml of ethyl acetate and 50 ml of a saturated solution of sodium hydrogen carbonate. The mixture is stirred for 30 minutes before being decanted. The organic phase recovered is washed with a saturated solution of sodium chloride then dried over sodium sulphate. The solvents are evaporated off and the foam obtained is purified on a silica column (eluent: $CH_2Cl_2$-EtOH/98-2 to 90-10). A light yellow coloured oil is obtained, which crystallizes from ether. After filtration on frit and washing with ether, a pale yellow coloured powder is obtained with a yield of 59%.

NMR $^1$H (δ ppm, DMSO): 1.39 (s, 9H); 4.17 (m, 2H); 6.4 (m, 2H); 6.82 (m, 2H); 7.07–7.36 (m, 3H); 7.59–7.73 (m, 4H); 11.7 (broad s, 1H).

4.4) N'-{4-[2-(aminomethyl)-1H-imidazol-4-yl]phenyl}thiophene-2-carboximidamide hydrochloride Intermediate 4.3 (3.1 g; 7 79 mmol) is suspended in 20 ml of ethyl acetate. Hydrochloric acid of concentration 4.4 M in ethyl acetate (80 ml; 0.35 mol) is added and the mixture obtained stirred at 22° C. for 18 hours. After concentration to dryness, the residue is taken up in ether before being reconcentrated to dryness. After stirring in isopentane then filtration on frit and rinsing of the solid in isopentane, a cream-coloured powder is obtained with a yield of 95%. Melting point: >260° C.

NMR $^1$H (δ ppm, DMSO): 4.47 (s, 2H); 7.37–7.39 (m, 1H); 7.59 (m, 2H); 8.05 (m, 2H); 8.18 (m, 3H); 9.08 (broad m, 3H); 9.94 (broad s, 1H); 11.6–11.8 (broad s, 1H).

4.5) N-(4-{2-[(cyclohexylamino)methyl]-1H-imidazol-4-yl}phenyl)thiophene-2-carboximidamide Intermediate 4.4 (800 mg; 1.96 mmol) is suspended in 30 ml of methanol in the presence of triethylamine (0.83 ml; 5.88 mmol). Cyclohexanone (0.25 ml; 2.35 mmol) is then added, then the mixture is stirred for three hours at 23° C. After the addition of sodium triacetoxyborohydride (500 mg; 2.35 mmol), the mixture is once again stirred at 23° C. for two hours. A saturated solution of potassium hydrogen sulphate is then added, then water in order to solubilize the precipitate which has formed. Finally, a saturated solution of sodium bicarbonate is added to the mixture obtained before quintuple extraction with ethyl acetate. The organic phase is then dried over sodium sulphate. The solvents are evaporated off and the foam obtained is purified on a silica column (eluent: $CH_2Cl_2$-EtOH—$NH_4OH$/92.5-5.5-2 to 90-7.5-2.5). A light yellow coloured oil is obtained, which crystallizes from ether. After filtration on frit and washing the solid with ether, a pale yellow coloured powder is obtained with a yield of 64%.

NMR $^1$H (δ ppm, DMSO): 1.02–1.22 (s, 5H); 1.52–1.84 (m, 5H); 2.37–2.42 (m, 1H); 3.75 (s, 2H); 6.41 (m, 2H); 6.82 (m, 2H); 7.08 (m, 1H); 7.36 (m, 1H); 7.59–7.74 (m, 4H); 11.7 (broad s, 1H). MH+=380.2.

4.6) N-(4-{2-[(cyclohexylamino)methyl]-1H-imidazol-4-yl}phenyl)thiophene-2-carboximidamide hydrochloride This compound is obtained from intermediate 4.5 according to an operating method analogous to that of Stage 1.5 of Example 1. Melting point: 234–235° C.

MH+=394.2.

The compounds of Examples 5 to 9 are prepared according to an operating method analogous to that described for the compound Example 4.

Example 5

N'-(4-{2-[2-(cyclohexylamino)ethyl]-1H-imidazol-4-yl}phenyl)thiophene-2-carboximidamide hydrochloride Melting point: 185–186° C. MH+=394.2.

Example 6

N'-(3{2-[cyclohexylamino)methyl]-1H-imidazol-4-yl}phenyl)thiophene-2-carboximidamide hydrochloride Melting point: >225° C. MH+=380.2.

Example 7

N'-[4-(2-{[cyclohexyl(methyl)amino]methyl}-1H-imidazol-4-yl)phenyl]thiophene-2-carboximidamide hydrochloride Melting point: 240–241° C.

Example 8

N'-(4{2-[(dibenzylamino)methyl]-1H-imidazol-4-yl}phenyl)thiophene-2-carboximidamide hydrochloride Melting point: 150-151° C. MH+=478.2.

Example 9

N'-(4-{2-[(benzylamino)methyl]-1H-imidazol-4-yl}phenyl)thiophene-2-carboximidamide hydrochloride Melting point: 228–229° C. MH+=388.1.

Example 10

N'-{3-[2-(aminomethyl)-1H-imidazol-4yl]phenyl}thiophene-2-carboximidamide hydrochloride

10.1) Tert-butyl [4-(3-nitrophenyl)-1H-imidazol-2-yl]methylcarbamate

This compound is prepared according to an operating method analogous to that described for Stage 4.1 of Example4, with 3-nitrophenacyl bromide replacing 4-azidophenacyl bromide. The expected compound is obtained in the form of a cream-coloured powder with a yield of 44%.

NMR $^1$H (δ ppm, DMSO): 4.96 (s, 2H); 7.69–7.75 (m, 4H); 7.90 (dd, 2H); 8.08 (dd, 2H). MH+=319.2.

10.2) Tert-butyl [4(3-aminophenyl)-1H-imidazol-2-yl]methylcarbamate

This compound is prepared according to an operating method analogous to that described for Stage 4.2 of Example 4, with intermediate 10.1 replacing intermediate 4.1. The expected compound is obtained in the form of a cream-coloured powder with a yield of 89%.

NMR $^1$H (δ ppm, DMSO): 1.39 (s, 9H); 4.2 (s, 2H); 6.43 (m, 1H); 6.84–7.01 (m, 3H); 7.26–7.34 (m, 2H). MH+=289.2.

10.3) Tert-butyl [4(3-{[(1E)-amino(thien-2-yl)methylene]amino}phenyl)-1H-imidazol-2-yl]methylcarbamate This compound is prepared according to an operating method analogous to that described for Stage 4.3 of Example 4, with intermediate 10.2 replacing intermediate 4.2. The expected compound is obtained in the form of a white powder with a yield of 68%.

NMR $^1$H (δ ppm, DMSO): 1.39 (s, 9H); 4.15 (m, 2H); 6.34–6.62 (m, 3H); 7.08–7.74 (m, 8H); 11.77 (s, 1H).

10.4) N'-{3[2-(aminomethyl)-1H-imidazol-4-yl]phenyl}thiophene-2-carboximidamide hydrochloride This compound is prepared according to an operating method analogous to that described for Stage 4.4 of Example 4, with intermediate 10.3 replacing intermediate 4.3. The expected compound is obtained in the form of a white powder with a yield of 98%. Melting point: >265° C.

NMR $^1$H (δ ppm, DMSO): 4.40 (s, 2H); 7.38–7.45 (m, 2H); 7.64–7.68 (m, 1H); 7.95 (m, 2H); 8.12–8.23 (m, 3H); 9.06 (broads, 4H); 9.96 (s, 1H); 11.81 (broad s, 1H).

Example 11

N'-{3[2-({[(1E)-amino(thien-2-yl)methylene]-amino}methyl)-1H-imidazol-4-yl]phenyl}thiophene-2-carboximidamide hydrochloride

11.1) N'-{3-[2-({[(1E)-amino(thien-2-yl)methylene]amino}methyl)-1H-imidazol-4-yl]phenyl}thiophene-2-carboximidamide This compound is prepared according to an operating method analogous to that described for Stage 4.3 of Example 4, with the compound of Example 10 replacing intermediate 4.2. The expected compound is obtained in the form of a cream-coloured powder with a yield of 80%.

MH+=407.2.

11.2) N'-{3[2({[(1E)-amino(thien-2yl)methylene]amino}methyl)-1H-imidazol-4-yl]phenyl}thiophene-2-carboximidamide hydrochloride This compound is obtained from intermediate 11.1 according to an operating method analogous to that of Stage 1.5 of Example 1. Melting point: >300° C.
MH+=407.2.

The compound of Example 12 is prepared according to an operating method analogous to that described for the compound of Example 11.

Example 12

N'-{4-[2-({[(1E)-amino(thien-2-yl)methylene]amino}methyl)-1H-imidazol-4-yl]phenyl}thiophene-2-carboximidamide hydrochloride Melting point: 227–228° C. MH+=407.2.

Example 13

N-{3[2-(2-cyclohexlethyl)-1H-imidazol-4-yl]phenyl}thiophene-2-carboximidamide hydrochloride 13.1) 2-(2-cyclohexylethyl)-4-(3-nitrophenyl)-1H-imidazole This compound is prepared according to an operating method analogous to that described for Stage 4.1 of Example 4, with cyclohexylethylcarboxylic acid and 3-nitrophenacyl bromide placing N-(tert-butoxycarbonyl)-glycine and 4-azidophenacyl bromide respectively. The expected compound is obtained in the form of a yellow powder with a yield of 26%.
MH+=300.2.

13.2) 3-[2(2-cyclohexylethyl)-1H-imidazol-4-yl]aniline

This compound is prepared according to an operating method analogous to that described for Stage 4.2 of Example 4, with intermediate 13.1 replacing intermediate 4.1. The expected compound is obtained in the form of a white powder with a yield of 93%. MH+=270.2.

13.3) N-{3-[2-(2-cyclohexylethyl)-1H-imidazol-4-yl]phenyl}thiophene-2-carboximidamide This compound is prepared according to an operating method analogous to that described for Stage 4.3 of Example 4, with intermediate 13.2 replacing intermediate 4.2. The expected compound is obtained in the form of a white powder with a yield of 20%. MH+=379.2.

13.4) N-{3[2-(2-cyclohexylethyl)-1H-imidazol-4-yl]phenyl}-thiophene-2-carboximidamide hydrochloride This compound is obtained from intermediate 13.3 according to an operating method analogous to that of Stage 1.5 of Example 1. Melting point: >191–193° C.
MH+=379.2.

The compounds of Examples 14 to 20 are prepared according to an operating method analogous to that described for the compound of Example 13.

Example 14

N'-{3-[2(1-pentylhexyl)-1H-imidazol-4-yl]phenyl}thiophene-2-carboximidamide hydrochloride Melting point: 163.3° C. MH+=423.2.

Example 15

N'-{4-[2-(2-cyclohexylethyl)-1H-imidazol-4-yl]phenyl}thiophene-2-carboximidamide hydrochloride Melting point: 196.2° C. MH+=379.2.

Example 16

N'-{3-[2-(cyclohexylmethyl)-1H-imidazol-4-yl]phenyl}thiophene-2-carboximidamide hydrochloride Pale yellow foam. MH+=365.2; r.t.=7.40 min.

Example 17

N'-{3-[2-(3-cyclohexylpropyl)-1H-imidazol-4-yl]phenyl}thiophene-2-carboximidamide hydrochloride Melting point: 180–181° C. MH+=393.2.

Example 48

N'-[3-(2-hexyl-1H-imidazol-4-yl)phenyl]thiophene-2-carboximidamide hydrochloride Pale yellow foam. MH+=353.2; r.t.=7.40 min.

Example 19

N{4-[2-(2-cyclohexylethyl)-1H-imidazol-4-yl]phenyl}N"-nitroguanidine hydrochloride Melting point: 185–186° C. MH+=357.2.

The compounds of Examples 20 to 23 are prepared according to an operating method analogous to that described for the compound of Example 4

Example 20

N'-(4-{2-[(cycloheptylamino)methyl]-1H-imidazol-4-yl}phenyl)thiophene-2-carboximidamide hydrochloride Melting point: 264–265° C.

Example 21

N'-(4-{2-[(methylamino)methyl]-1H-imidazol-4-yl}phenyl)thiophene-2-carboximidamide hydrochloride Melting point: >250° C.

Example 22

N'-(4-{2-[(cyclobutylamino)methyl]-1H-imidazol-4-yl}phenyl)thiophene-2-carboximidamide hydrochloride Melting point: 263–264° C.

Example 23

N'[4-(2-{[(2,2-diphenylethyl)amino]methyl}-1H-imidazol-4-yl)phenyl]thiophene-2-carboximidamide hydrochloride Melting point: >250° C. [the reagent used in the last stage, 3,3-diphenylpropanal, is prepared from commercial compounds adapted according to a protocol similar to that described in *J. Org. Chem.* (1990), 55(17), 5078–88].

The compound of Example 24 is prepared according to an operating method analogous to that described for the compound of Example 11.

Example 24

N'-{3-[2-(2{[(1E)-amino(thien-2-yl)methylene]amino}ethyl)-1H-imidazol-4-yl]phenyl}thiophene-2-carboximidamide hydrochloride Melting point: >245° C.

The compounds of Examples 25 to 27 are prepared according to an operating method analogous to that described for the compound of Example 13

Example 25

N'-(3-{2-[(phenylthio)methyl]-1H-imidazol-4-yl}phenyl)thiophene-2-carboximidamide hydrochloride This compound is obtained in the form of a pale yellow foam. MH+=391.1; r.t.=7.30 min.

Example 26

N'-(4-{2-[(phenylthio)methyl]-1H-imidazol-4-yl}phenyl)thiophene-2-carboximidamide hydrochloride This compound is obtained in the form of a pale yellow foam. MH+=391.1; r.t.=7.30 min.

Example 27

N'-{3-[2-(4-isobutylbenzyl)-1H-imidazol-4-yl]phenyl}thiophene-2-carboximidamide hydrochloride Melting point: 214–216° C. [the preparation of the initial compound, (4-isobutylphenyl)acetic acid, was described in the PCT application WO 02/102375—see Example 1, Stage 1 of this document].

Pharmacological Study of the Products of the Invention

Binding Test on the Sodium Channels of Rat Cerebral Cortices

The test consists of measuring the interaction of the compounds vis-à-vis the binding of tritiated batrachotoxin to the voltage-dependent sodium channels according to the protocol described by Brown (*J. Neurosci.* (1986), 6, 2064–2070).

Preparation of the Homogenates of Rat Cerebral Cortices

The cerebral cortices of Sprague Dawley rats of 230–250 g (Charles River, France) are removed, weighed and homogenized using a Potter grinder equipped with a Teflon piston (10 return strokes) in 10 volumes of isolation buffer, the composition of which is as follows (sucrose 0.32 M; $K_2HPO_4$ 5 mM; pH7.4). The homogenate undergoes a first centrifugation at 1000 g for 10 minutes. The supernatant is removed and centrifuged at 20000 g for 15 minutes. The pellet is taken up in the isolation buffer and centrifuged at 20000 g for 15 minutes. The pellet obtained is resuspended in incubation buffer (50 mM HEPES; 5.4 mM KCl; 0.8 mM $MgSO_4$; 5.5 mM glucose; 130 mM choline chloride pH7.4) then aliquoted and stored at −80° C. until the day of the assay. The final protein concentration is comprised between 4 and 8 mg/ml. The assay of the proteins is carried out using a kit marketed by BioRad (France).

Measurement of the Tritiated Batrachotoxin Binding

The binding reaction is carried out by incubating for 1 hour 30 minutes at 25° C. 100 µl of rat cortex homogenate containing 75 µg of proteins with 100 µl of [$^3$H] batrachotoxin-A 20-alpha benzoate (37.5 Ci/mmol, NEN) at 5 nM (final concentration), 200 µl of tetrodotoxin at 1 µM (final concentration) and scorpion venom at 40 µg/ml (final concentration) and 100 µl of incubation buffer alone or in the presence of the products to be tested at the different concentrations. The non-specific binding is determined in the presence of 300 µM of veratridine and the value of this non-specific binding is subtracted from all the other values. The samples are then filtered using a Brandel (Gaithersburg, Md., USA), using Unifilter GF/C plates preincubated with 0.1% of polyethyleneimine (20 µl/well) and rinsed twice with 2 ml of filtration buffer (5 mM HEPES; 1.8 mM $CaCl_2$; 0.8 mM $MgSO_4$; 130 mM choline chloride; pH7.4). After the addition of 20 µl of Microscint 0®, the radioactivity is counted using a liquid scintillation counter (Topcount, Packard). The measurement is carried out in duplicate. The results are expressed as a % of the specific binding of the tritiated batrachotoxin with respect to the control.

Results

The compounds of Examples 1 to 9, 11 to 20 and 22 to 27 described above all have an $IC_{50}$ lower than or equal to 10 µM.

Study of the Effects on the Neuronal Constitutive NO Synthase of Rat Cerebellum

The inhibiting activity of the products of the invention is determined by measuring their effects on the conversion by the NO synthase of [$^3$H]L-arginine to [$^3$H]L-citrulline in accordance with the modified method of Bredt and Snyder (*Proc. Natl. Acad. Sci. USA*, (1990) 87:682–685).

Preparation of the Homogenates of Rat Cerebellums

The cerebellums of Sprague Dawley rats (300 g—Charles River) are rapidly removed, weighed and homogenized in 5 volumes of extraction buffer (50 mM HEPES, 1 mM EDTA, pH7.4, pepstatin A 10 mg/ml, leupeptin 10 mg/ml). The homogenates are then centrifuged at 35000 g for 1 hour at 4° C. The supernatants are then passed on to a DOWEX 50W-X8 resin column, sodium form taken up in the extraction buffer, in order to eliminate the endogenous arginine. The preparation obtained is aliquoted and stored at −80° C.

Assay of the Neuronal NOS Activity

The incubation buffer is composed of 100 mM of HEPES (pH7.4), 2 mM of EDTA, 152.5 mM of $CaCl_2$, 2 mM of dithiotreitol, 2 mM of reduced NADPH, 10 μg/ml of calmodulin, 10 μM of FAD, 10 μM of FMN, and 10 μM of BH4. The products to be tested are diluted in this buffer. The reaction is carried out by incubating for 15 minutes at 37° C. 100 μl of incubation buffer containing or not containing the inhibitors, 25 μl of a solution containing 62.5 nM of [$^3$H] L-arginine (specific activity: 56.4 Ci/mmol, Perkin Elmer) and 25 μM of non-radioactive L-arginine, 25 μl of incubation buffer, and 50 μl of enzyme preparation diluted 10 times in 50 mM HEPES buffer. The reaction is stopped with 2 ml of 20 mM HEPES buffer, pH5.5, containing 2 mM of EDTA. All of the samples are passed on to a 1 ml DOWEX 50W-X8 resin column, sodium form, taken up in the stopping buffer. After the addition of 16 ml of scintillating liquid (Ultima Gold, Packard), the radioactivity is quantified by a liquid scintillation counter (Winspectral 1410, Wallac). The measurements are carried out in duplicate. Each series of measurement comprises 2 tubes not containing enzyme (reaction blank the value of which is subtracted from each measurement) and 2 tubes not containing inhibitors (reaction control). The results are expressed as enzyme reaction inhibition percentages (reaction control value).

Results

The compounds of Examples 1 to 13, 15, 16 and 18 to 26 described above all present an $IC_{50}$ lower than or equal to 10 μM.

The invention claimed is:

1. A compound of the formula

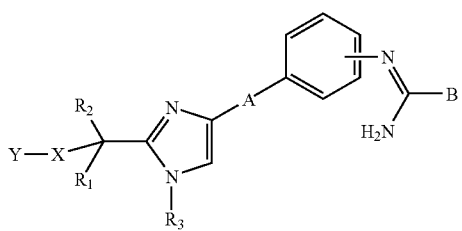

(I)

in the form of racemic, enantiomeric mixture of any combination of these forms, wherein $R_1$ is selected from the group consisting of hydrogen, alkyl, cycloalkyl, cycloalkylalkyl, aryl and aralkyl, the aromatic ring of which is optionally substituted from one to 3 times by a member chosen independently selected from the group consisting of halogen, alkyl and alkoxy;

$R_2$ is selected from the group consisting of hydrogen and alkyl;

X is selected from the group consisting of a bond and, alkylene of 1 to 5 carbon atoms;

Y is selected from the group consisting of hydrogen, cycloalkyl, $NR_4R_5$, $OR_{14}$, $SR_{15}$ and

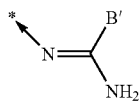

or Y is selected from the group consisting of aryl optionally substituted from one to 3 times by a member independently selected from the group consisting of halogen, alkyl and alkoxy;

A is selected from the group consisting of a bond or phenylene;

B and B' are independently selected from the group consisting of alkyl, cycloalkyl, —$NR_6R_7$, —$SR_8$, carbocyclic aryl and heterocyclic aryl with 5 to 6 ring members having 1 to 4 heteroatoms selected from the group consisting of O, S and N, said carbocyclic and heterocyclic aryl being optionally substituted by one to three members independently selected from the group consisting of alkyl, alkenyl and alkoxy, $R_3$ is selected from the group selected from the group consisting of hydrogen, alkyl and aralkyl;

$R_4$ is selected from the group consisting of hydrogen, alkyl, cycloalkyl, cycloalkylalkyl, —C(O)—$R_9$, —C(O)$OR_9$, —C(O)$NHR_9$, —$SO_2R_9$ and aralkyl, the aromatic ring of which is optionally substituted one to 3 times by a member independently selected from the group consisting of hydrogen, alkyl and alkoxy, or $R_4$ is bis-phenylalkyl, $R_5$ is selected from the group consisting of hydrogen, alkyl, aryl and aralkyl, or $R_4$ and $R_5$ form with the nitrogen atom which carries them a non-aromatic heterocyclic of five to seven ring members having 1 to 2 heteroatoms, the elements for completing the heterocycle being independently selected from the group consisting of —$CHR_{10}$—, —$NR_{11}$—, —O— and —S—;

$R_6$ and $R_7$ are selected from the group consisting of hydrogen, alkyl, alkenyl and alkynyl;

or $R_6$ is —$NO_2$ and $R_7$ is hydrogen, or $R_6$ and $R_7$ form with the nitrogen atom which carries them a non-aromatic heterocyclic with five to six ring members, the elements for completing the heterocycle being independently selected from the group consisting of —$CH_2$—, —$NR_{12}$—, —O— and —S—;

$R_8$ is alkyl of 1 to 6 carbon atoms optionally substituted from one to 3 times by a member independently selected from the group consisting of halogen, —OH, amino, cyano and aryl;

$R_9$ is selected from the group consisting of alkyl, haloalkyl, cycloalkyl, cycloalkylalkyl, carbocyclic and heterocyclic aralkyl and aryl, the aromatic ring of which is optionally substituted from one to 3 times by a member independently selected from the group consisting of halogen, alkyl and alkoxy;

$R_{10}$ is selected from a group consisting of hydrogen, alkyl and aryl optionally substituted from one to 3 times by a member independently selected from the group consisting of halogen, alkyl and alkoxy, $R_{11}$ is selected from the group consisting of hydrogen, alkyl, cycloalkyl, cycloalkylalkyl, —C(O)$R_{13}$, —C(O)$OR_{13}$, —$SO_2R_{13}$, —C(O)$NHR_{13}$ and the aryl and aralkyl, the aromatic ring of which is optionally substituted from one to 3 times by a member independently selected from the group consisting of halogen, alkyl and alkoxy;

$R_{12}$ is selected from the group consisting of hydrogen and alkyl;

$R_{13}$ is selected from the group consisting of alkyl, haloalkyl and carbocyclic and heterocyclic aralkyl or aryl, the aromatic ring of which is optionally substituted one to 3 times by a member independently selected from the group consisting of halogen, alkyl and alkoxy;

R$_{14}$ is selected from the group consisting of alkyl, phenyl and aralkyl; and R$_{15}$ is selected from the group consisting of alkyl, phenyl and aralkyl;

it being understood:
that alkyl or alkoxy, unless otherwise specified, has 1 to 12 carbon atoms;
that alkenyl or alkynyl, unless otherwise specified, has 2 to 6 carbon atoms;
that cycloalkyl, unless otherwise specified, has 3 to 7 carbon atoms;
and a salt of a compound of formula (I).

2. A compound of claim 1, wherein X is a bond or alkylene of 1 to 5 carbon atoms and Y is —NR$_4$R$_5$; and a salt thereof.

3. A compound of claim 1, wherein X is a bond or alkylene of 1 to 5 carbon atoms and Y is

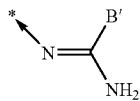

and a salt thereof.

4. A compound of claim 1, wherein X is a bond or alkylene of 1 to 5 carbon atoms and Y is cycloalkyl or aryl optionally substituted one to 3 times by a member independently selected from the group consisting of halogen, alkyl and alkoxy; and a salt thereof.

5. A compound of claim 1, selected from the group consisting of
butyl-2-[4-(4-{[(1Z)-amino(thien-2-yl)methylene]amino}phenyl)-1H-imidazol-2-yl]ethylcarbamate;
butyl-2-[4-(3-{[(1E)-amino(thien-2-yl)methylene]-amino}phenyl)-1H-imidazol-2-yl]ethylcarbamate;
butyl-2-[4-(4'-{[(1Z)amino(thien-2-yl)methylene]amino}-1,1'-biphenyl-4-yl)-1H-imidazol-2-yl]ethylcarbamate;
N'-(4-{2-[(cyclohexylamino)methyl]-1H-imidazol-4-yl}phenyl)thiophene-2-carboximidamide;
N'-(4-{2-[2-(cyclohexylamino)ethyl]-1H-imidazol-4-yl}phenyl)thiophene-2-carboximidamide;
N'-(3-{2-[(cyclohexylamino)methyl]-1H-imidazol-4-yl}phenyl)thiophene-2-carboximidamide;
N'-[4-(2-{[cyclohexyl(methyl)amino]methyl}-1H-imidazol-4-yl)phenyl]thiophene-2-carboximidamide;
N'-(4-{2-[(dibenzylamino)methyl]-1H-imidazol-4-yl}phenyl)thiophene-2-carboximidamide;
N'(4-{2-[(benzylamino)methyl]-1H-imidazol-4-yl}phenyl)thiophene-2-carboximidamide;
N'-{3-[2-(aminoethyl)-1H-imidazol-4-yl]phenyl}thiophene-2-carboximidamide;
N'-{3-[2-({[(1E)-amino(thien-2-yl)methylene]-amino}methyl)-1H-imidazol-4-yl]phenyl}thiophene-2-carboximidamide;
N'-{4-[2-({[(1E)-amino(thien-2-yl)methylene]amino}methyl)-1H-imidazol-4-yl]phenyl}thiophene-2-carboximidamide;
N-{3-[-2-(2-cyclohexylethyl)-1H-imidazol-4-yl]phenyl}thiophene-2-carboximidamide;
N'-{3-[2-(1-pentylhexyl)-1H-imidazol-4-yl]phenyl}thiophene-2-carboximidamide;
N'-{4-[2-(2-cyclohexylethyl)-1H-imidazol-4-yl]phenyl}thiophene-2-carboximidamide;
N'-{3-[2-(cyclohexylmethyl)-1H-imidazol-4-yl]phenyl}thiophene-2-carboximidamide;
N'-{3-[2-(3-cyclohexylpropyl)-1H-imidazol-4-yl]phenyl}thiophene-2-carboximidamide;
N'-[3-(2-hexyl-1H-imidazol-4-yl)phenyl]thiophene-2-carboximidamide;
N-{4-[2-(2-cyclohexylethyl)-1H-imidazol-4-yl]phenyl}-N''-nitroguanidine;
N'-(4-{2-[(cycloheptylamino)methyl]-1H-imidazol-4-yl}phenyl)thiophene-2-carboximidamide;
N'-(4-{2-[(methylamino)methyl]-1H-imidazol-4-yl}phenyl)thiophene-2-carboximidamide;
N'-(4-{2-[(cyclobutylamino)methyl]-1H-imidazol-4-yl}phenyl)thiophene-2-carboximidamide;
N'-[4-(2-{[(2,2-diphenylethyl)amino]methyl}-1H-imidazol-4-yl)phenyl]thiophene-2-carboximidamide;
N'-{3-[2-(2-{[(1E)-amino(thien-2-yl)methylene]amino}ethyl)-1H-imidazol-4-yl]phenyl}thiophene-2-carboximidamide;
N'-(3-{2-[(phenylthio)methyl]-1H-imidazol-4-yl}phenyl)thiophene-2-carboximidamide;
N'-(4-{2-[(phenylthio)methyl]-1H-imidazol-4-yl}phenyl)thiophene-2-carboximidamide and;
N'-{3-[2-(4-isobutylbenzyl)-1H-imidazol-4-yl]phenyl}thiophene-2-carboximidamide;
and a salt thereof.

6. A pharmaceutical composition containing, as active ingredient, a compound of claim 1 and an inert pharmaceutical acceptable excipient.

7. A method of treating pain in warm-blooded animals comprising administering to warm-blooded animals in need thereof an effective amount of a compound of claim 1.

* * * * *